United States Patent

Hagiwara et al.

[11] Patent Number: 5,567,560
[45] Date of Patent: Oct. 22, 1996

[54] TRIPHENYLAMINE DERIVATIVE CHARGE–TRANSPORTING MATERIAL CONTAINING ELECTROPHOTOGRAPHIC PHOTORECEPTOR

[75] Inventors: Toshimitsu Hagiwara; Hiroshi Sugiyama; Yoshimasa Matsushima; Tohru Kobayashi, all of Kanagawa, Japan

[73] Assignee: Takasago International Corporation, Tokyo, Japan

[21] Appl. No.: 443,661

[22] Filed: May 18, 1995

Related U.S. Application Data

[62] Division of Ser. No. 333,295, Nov. 1, 1994.

[30] Foreign Application Priority Data

Nov. 2, 1993  [JP]  Japan ................... 5-295965

[51] Int. Cl.[6] .................... G03G 5/047
[52] U.S. Cl. .................... 430/59; 430/73
[58] Field of Search ................... 430/59, 73

[56] References Cited

U.S. PATENT DOCUMENTS

| | | | |
|---|---|---|---|
| 4,606,988 | 8/1986 | Sasaki . | |
| 4,777,296 | 10/1988 | Sasaki . | |
| 5,024,912 | 6/1991 | Neishi et al. | 430/73 |
| 5,166,019 | 11/1992 | Ueda et al. | 430/73 |
| 5,183,718 | 2/1993 | Ueda . | |
| 5,213,924 | 5/1993 | Sakamoto | 430/96 |
| 5,213,926 | 5/1993 | Hanatani et al. | 430/59 |
| 5,246,808 | 9/1993 | Hanatani et al. . | |

FOREIGN PATENT DOCUMENTS

| | | |
|---|---|---|
| 60-175052 | 9/1985 | Japan . |
| 62-120346 | 6/1987 | Japan . |
| 1217357 | 8/1989 | Japan . |
| 2226159 | 9/1990 | Japan . |

OTHER PUBLICATIONS

Diamond, Arthur S. (1991) *Handbook of Imaging Materials*. New York: Marcel–Dekker, Inc. pp. 401–420.
Chemical Abstracts 121:87570 (1994).
Chemical Abstracts, vol. 114, No. 22 (Jun. 3, 1991), Abstract No. 218073.

*Primary Examiner*—Christopher D. Rodee
*Attorney, Agent, or Firm*—Sughrue, Mion, Zinn, Macpeak & Seas

[57] ABSTRACT

A triphenylamine derivative, a charge-transporting material comprising the triphenylamine derivative, and an electrophotographic photoreceptor containing a charge-transporting layer comprising the triphenylamine derivative are disclosed, wherein the triphenylamine derivative is represented by the following general formula (1):

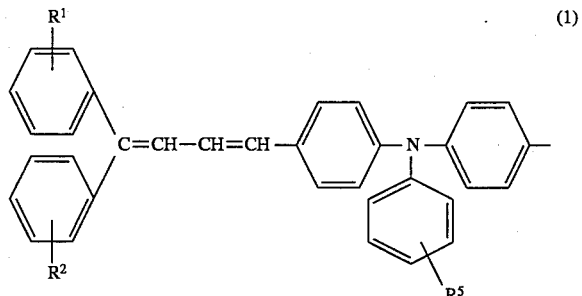

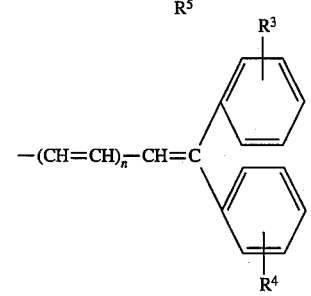

wherein $R^1$, $R^2$, $R^3$, $R^4$, and $R^5$ may be the same or different and each represents a hydrogen atom, a lower alkyl group, an alkoxy group, a halogen atom, or an aryl group which may have a substituent, or $R^1$ and $R^2$ and/or $R^3$ and $R^4$ may be taken together to form a ring, and n represents 0 or 1.

9 Claims, No Drawings

TRIPHENYLAMINE DERIVATIVE CHARGE-TRANSPORTING MATERIAL CONTAINING ELECTROPHOTOGRAPHIC PHOTORECEPTOR

This is a divisional of application Ser. No. 08/333,295 filed Nov. 1, 1994 pending.

FIELD OF THE INVENTION

The present invention relates to a novel triphenylamine derivative represented by the following general formula (1):

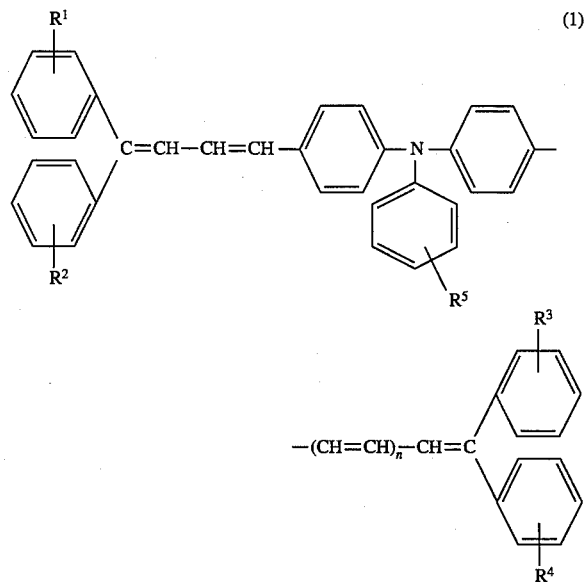

wherein $R^1$, $R^2$, $R^3$, $R^4$, and $R^5$ may be the same or different and each represents a hydrogen atom, a lower alkyl group, an alkoxy group, a halogen atom, or an aryl group which may have a substituent, or $R^1$ and $R^2$ and/or $R^3$ and $R^4$ may be taken together to form a ring, and n represents 0 or 1. This invention further relates to a charge-transporting material comprising the derivative and to an electrophotographic photoreceptor containing a charge-transporting layer comprising the charge-transporting material.

BACKGROUND OF THE INVENTION

Inorganic photoconductive materials recently in use include amorphous silicon, amorphous selenium, cadmium sulfide, zinc oxide, and the like. However, some of these materials are expensive because of difficulties in production thereof, while others are toxic and disadvantageous from the standpoint of environmental protection.

On the other hand, as organic photoconductors, ones of the type comprising, in particular, a charge-generating material and a charge-transporting material which respectively perform their functions are proposed extensively (e.g., U.S. Pat. No. 3,791,826). In this type, there is the possibility that a high-sensitivity electrophotographic photoreceptor might be obtained by using a substance which efficiently generates carriers (The term "carriers" means "charges"; the same applies hereinafter) as the charge-generating material in combination with a substance having high carrier-transporting ability as the charge-transporting material.

Of these materials, the charge-transporting material is required to efficiently receive the carriers generated in the charge-generating material upon illumination in an electric field and permit them to rapidly move through the photosensitive layer to extinguish the surface charges promptly. The speed at which carriers move per unit electric field is called carrier mobility. A high carrier mobility means that carriers rapidly move in the charge-transporting layer. Any charge-transporting substance has its intrinsic carrier mobility and, hence, it is necessary that for attaining a high carrier mobility, a material having a high carrier mobility be employed. However, the attainable carrier mobilities have not yet reached a sufficient level.

Further, in the case of applying a charge-transporting substance after dissolving it in an organic solvent along with a binder polymer, it is necessary to form a thin homogeneous organic coating film free from crystallization and pinhole formation. This is because when a high electric field is applied to the thin film obtained, the part having microcrystals or pinholes undergoes dielectric breakdown or causes noise.

In addition to the satisfactory properties of the charge-generating substance and of the charge-transporting substance, it is also important that carriers should be efficiently injected from the charge-generating substance into the charge-transporting substance, i.e., from the charge-generating layer into the charge-transporting layer. This injection of charges depends on the properties of the interface between the charge-generating substance (or charge-generating layer) and the charge-transporting substance (or charge-transporting layer) and varies with combinations of various substances. Since a charge-transporting material should meet various requirements as described above, charge-transporting substances having a variety of properties are being developed.

Among conventional charge-transporting materials, the styryl compound represented by the formula

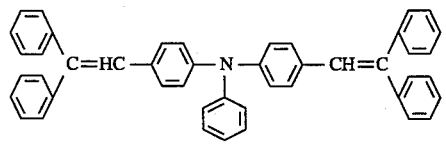

is, for example, proposed in JP-A-60-174749. (The term "JP-A" as used herein means an "unexamined published Japanese patent application.")

Moreover, a styryl compound represented by the following general formula (2)

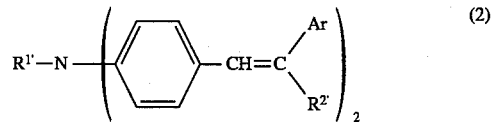

(wherein $R^{1'}$ represents an optionally substituted alkyl group or an optionally substituted aryl group, $R^{2'}$ represents a hydrogen atom, an optionally substituted alkyl group, or an optionally substituted aryl group, and Ar represents an optionally substituted aryl group) is proposed in JP-A-60-175052.

Furthermore, compounds similar to the compound (2) above are proposed in, for example, JP-A-62-120346, JP-A-1-217357, JP-A-4-57056, and JP-A-4-292663.

The demand for charge-transporting materials is growing more and more, with which there is a desire for a newer material which is capable of satisfying various requirements.

In JP-A-4-57056, for example, there is a description to the effect that the compound K specified below partly separated out as crystals during the preparation of a photoreceptor because of the poor solubility of the compound.

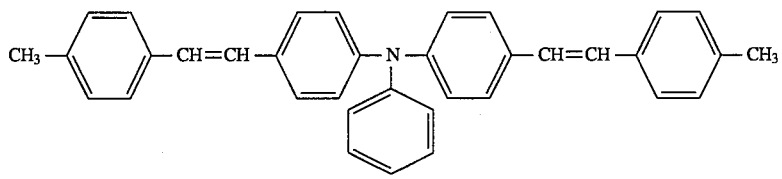

(K)

There has hence been a desire for the development of a new material which not only is satisfactory in such solubility and other properties but also is capable of attaining a high carrier mobility.

SUMMARY OF THE INVENTION

Accordingly, an object of the present invention is to provide a novel charge-transporting material which gives a stable film attaining a high carrier mobility and which, when used in an electrophotographic photoreceptor, is also excellent in various properties.

As a result of intensive studies made by the present inventors on a wide range of compounds under these circumstances, they have found that the problems described above can be overcome with a triphenylamine derivative which has a diphenylbutadienyl-framework substituent bonded to one of the phenyl groups of triphenylamine and further has a diphenylbutadienyl- or diphenylvinyl-framework substituent bonded to another phenyl group and which is represented by the following general formula (1):

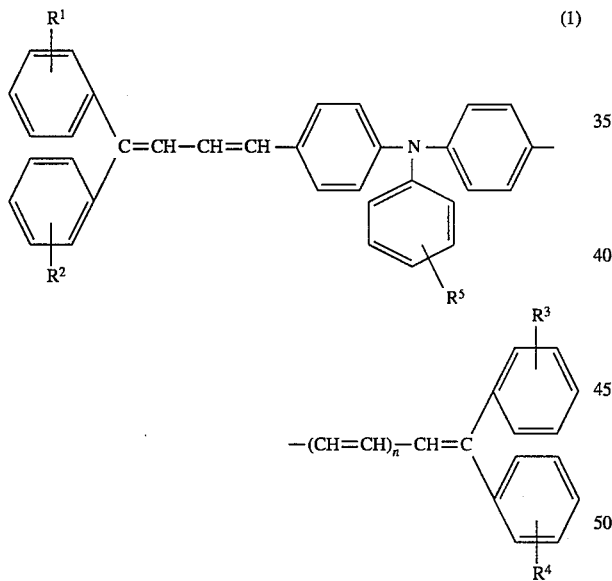

wherein $R^1$, $R^2$, $R^3$, $R^4$, and $R^5$ may be the same or different and each represents a hydrogen atom, a lower alkyl group, an alkoxy group, a halogen atom, or an aryl group which may have a substituent, or $R^1$ and $R^2$ and/or $R^3$ and $R^4$ may be taken together to form a ring, and n represents 0 or 1. The present invention has been completed based on this finding.

That is, the present inventors have found that the triphenylamine derivative (1) has good solubility in binder polymers, suffers neither crystallization nor pinhole formation, and is capable of attaining a high carrier mobility, and that a photoreceptor employing this compound is high in sensitivity and low in residual potential.

The present invention therefore relates to the novel triphenylamine derivative represented by the general formula (1) given above, a charge-transporting material comprising the compound represented by general formula (1), and an electrophotographic photoreceptor containing a charge-transporting layer comprising the charge-transporting material.

DETAILED DESCRIPTION OF THE INVENTION

In the compound (1) of this invention, $R^1$, $R^2$, $R^3$, $R^4$, and $R^5$ may be the same or different and each represents a hydrogen atom, a lower alkyl group, an alkoxy group, a halogen atom, or an aryl group which may have a substituent, or $R^1$ and $R^2$ or $R^3$ and $R^4$ may be taken together to form a ring. Examples of the lower alkyl group include alkyl groups having 1 to 4 carbon atoms, e.g., methyl, ethyl, n-propyl, isopropyl, n-butyl, and isobutyl, with methyl or ethyl being especially preferred.

Examples of the alkoxy group include alkoxy groups having 1 to 4 carbon atoms, e.g., methoxy, ethoxy, propoxy, and butoxy.

Examples of the halogen atom include fluorine, chlorine, bromine, and iodine.

Examples of the aryl group which may have a substituent include phenyl, lower-alkyl-substituted phenyl groups, e.g., p-tolyl and 2,4-dimethylphenyl, lower-alkoxy-substituted phenyl groups, e.g., p-methoxyphenyl, and halogen-substituted phenyl groups, e.g., p-chlorophenyl.

$R^1$ and $R^2$ or $R^3$ and $R^4$ may be taken together to form a ring such as substituents forming a 5- to 7-membered ring. Specifically, examples of the group formed by $R^1$ and $R^2$ or $R^3$ and $R^4$ include the single bond, 2,2'-methylene, 2,2'—S—, 2,2'—O—, 2,2'—N(Ph)— (wherein Ph is a phenyl group), 2,2'-ethylene, 2,2'-vinylene, and 2,2'-phenylene. That is, these groups are represented by the following structural formula:

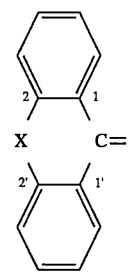

(wherein X represents a single bond, a methylene group, an oxygen atom, a sulfur atom, a phenylimino group, an ethylene group, a vinylene group or a phenylene group).

Preferred examples of the compound (1) of this invention include the compounds Shown in Table 1 below, but the compound (1) is not limited thereto.

TABLE 1

| Exemplified Compound | n | R¹ | R² | R³ | R⁴ | R⁵ |
|---|---|---|---|---|---|---|
| 1 | 0 | H | H | H | H | H |
| 2 | 1 | H | H | H | H | H |
| 3 | 0 | 4-Me | 4-Me | 4-Me | 3-Me | H |
| 4 | 0 | 4-Me | 4-Me | 4-Me | 4-Me | H |
| 5 | 1 | 4-Me | 4-Me | 4-Me | 4-Me | H |
| 6 | 1 | 4-Me | H | 4-Me | H | H |
| 7 | 0 | H | H | 4-Me | 4-Me | H |
| 8 | 1 | 3-Me | H | 3-Me | H | H |
| 9 | 0 | H | H | 3-Me | 3-Me | H |
| 10 | 0 | H | H | 4-Cl | 4-Cl | H |
| 11 | 1 | H | H | H | H | 4-Me |
| 12 | 0 | 4-Me | 4-Me | 4-Me | 4-Me | 4-Me |
| 13 | 1 | 4-Me | 4-Me | 4-Me | 4-Me | 4-Me |
| 14 | 1 | 3-Me | H | 3-Me | H | 4-Me |
| 15 | 1 | 4-Me | H | 4-Me | H | 4-Me |
| 16 | 1 | H | H | H | H | 4-Et |
| 17 | 1 | H | H | H | H | 4-MeO |
| 18 | 1 | 4-Me | 4-Me | 4-Me | 4-Me | 4-MeO |
| 19 | 1 | 4-Me | H | 3-Me | H | 4-MeO |
| 20 | 1 | 4-Me | H | 4-Me | H | 4-MeO |
| 21 | 1 | 3-Me | H | 3-Me | H | 4-MeO |
| 22 | 1 | H | H | H | H | 4-(p-Tol) |
| 23 | 1 | 4-Me | 4-Me | 4-Me | 4-Me | 4-(p-Tol) |
| 24 | 1 | 4-Me | H | 4-Me | H | 4-(p-Tol) |
| 25 | 1 | 3-Me | H | 3-Me | H | 4-(p-Tol) |
| 26 | 1 | H | H | H | H | 4-Br |
| 27 | 1 | 4-Me | 4-Me | 4-Me | 4-Me | 4-Br |
| 28 | 1 | 4-Me | H | 4-Me | H | 4-Br |
| 29 | 1 | 3-Me | H | 3-Me | H | 4-Br |
| 30 | 1 | 4-Cl | 4-Cl | 4-Cl | 4-Cl | H |
| 31 | 0 | 4-Me | 4-Me | H | H | H |
| 32 | 1 | 4-Me | 4-Me | 3-Me | 3-Me | H |
| 33 | 0 | 3-Me | 3-Me | H | H | H |
| 34 | 0 | 4-Me | 4-Me | H | H | 4-Me |
| 35 | 0 | H | H | 4-Me | 4-Me | 4-Me |
| 36 | 1 | 4-Me | 4-Me | H | H | H |
| 37 | 1 | 3-Me | 3-Me | H | H | H |
| 38 | 1 | 4-Me | 4-Me | H | H | 4-Me |
| 39 | 1 | 4-Me | 4-Me | H | H | 4-MeO |
| 40 | 1 | 4-Me | 4-Me | Cl | Cl | H |
| 41 | 0 | 2-CH₂CH₂-2' | | H | H | H |
| 42 | 1 | 2-CH₂CH₂-2' | | H | H | H |
| 43 | 0 | 2-CH₂CH₂-2' | | 4-Me | 4-Me | H |
| 44 | 1 | 2-CH₂CH₂-2' | | 2-CH₂CH₂-2' | | H |
| 45 | 1 | 2-CH₂-2' | | 2-CH₂-2' | | H |
| 46 | 1 | 2-O-2' | | 2-O-2' | | H |
| 47 | 1 | 2-S-2' | | 2-S-2' | | H |
| 48 | 1 | 2-N(Ph)-2' | | 2-N(Ph)-2' | | H |
| 49 | 1 | 2-CH=CH-2' | | 2-CH=CH-2' | | H |
| 50 | 1 | 2-2' | | 2-2' | | H |
| 51 | 1 | (biphenyl-2,2') | | (biphenyl-2,2') | | H |
| 52 | 1 | 2-CH₂CH₂-2' | | 2-CH₂CH₂-2' | | 4-Me |
| 53 | 1 | 2-CH₂-2' | | 2-CH₂-2' | | 4-Me |
| 54 | 1 | 2-O-2' | | 2-O-2' | | 4-Me |
| 55 | 1 | 2-S-2' | | 2-S-2' | | 4-Me |
| 56 | 1 | 2-N(Ph)-2' | | 2-N(Ph)-2' | | 4-Me |
| 57 | 1 | 2-CH=CH=2' | | 2-CH=CH-2' | | 4-Me |
| 58 | 1 | 2-2' | | 2-2' | | 4-Me |

The abbreviations given in the table have the following meanings.

4-Me: methyl substituent in the 4-position of phenyl

3-Me: methyl substituent in the 3-position of phenyl

4-Cl: chlorine atom substituent in the 4-position of phenyl

4-Et: ethyl substituent in the 4-position of phenyl

4-MeO: methoxy substituent in the 4-position of phenyl 4-(p-Tol): p-tolyl substituent in the 4-position of phenyl 4-Br: bromine atom substituent in the 4-position of phenyl Of the triphenylamine derivatives (1) of this invention, the compound in which n=1 (1a) can be synthesized according to, for example, the following reaction scheme 1.

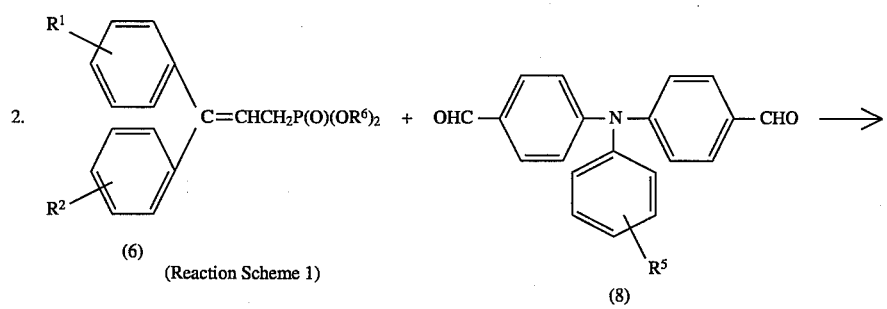

(Reaction Scheme 1)

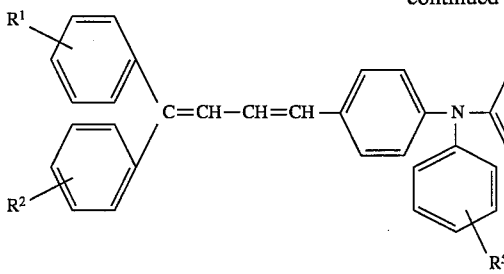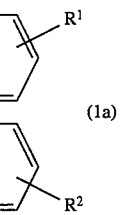

(1a)

(In the scheme, $R^1$, $R^2$, and $R^5$ have the same meanings as defined above, and $R^6$ represents a lower alkyl group.) It is especially preferred that $R^6$ be methyl or ethyl.

That is, the desired compound is easily produced by reacting a 4,4'-diformyltriphenylamine derivative (8) with a 3,3-diarylallylphosphorous acid dialkyl ester (6) in an amount of 2 mol per mol of the compound (8) in the presence of a base at a temperature between room temperature and around 80° C.

Examples of the base include sodium hydroxide, sodium amide, and metal alkoxides, e.g., sodium methoxide, sodium tert-butoxide, and potassium tert-butoxide.

As a solvent, use may be made of a lower alcohol, e.g., methanol or ethanol, an ether, e.g., 1,2-dimethoxyethane, diethyl ether, tetrahydrofuran, or dioxane, a hydrocarbon, e.g., toluene or xylene, an aprotic polar solvent, e.g., dimethyl sulfoxide, N,N-dimethylformamide, N,N-dimethylacetamide, or N-methylpyrrolidone, or a mixture thereof.

The 4,4'-diformyltriphenylamine derivative (8) can be easily obtained by subjecting a triphenylamine derivative (7) to the Vilsmeier-Haack reaction with heating using an excess of DMF (N,N-dimethylformamide), MFA (N-methylformanilide), or the like and an excess of phosphoryl chloride, phosgene, thionyl chloride, or the like (reaction scheme 2).

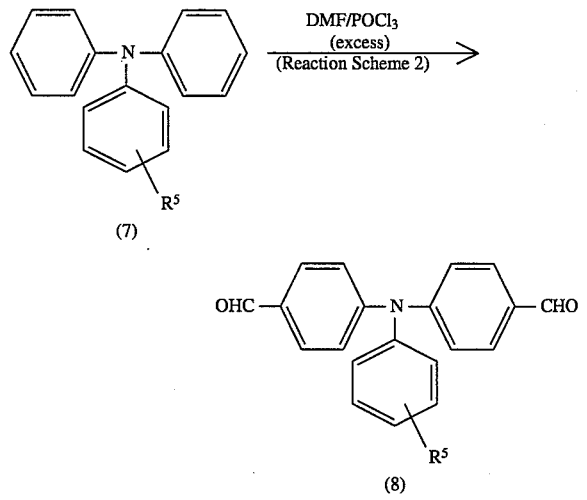

(In the scheme, $R^5$ has the same meaning as defined above.)

Further, the 3,3-diarylallylphosphorous acid dialkyl ester (6) can be obtained according to reaction scheme 3.

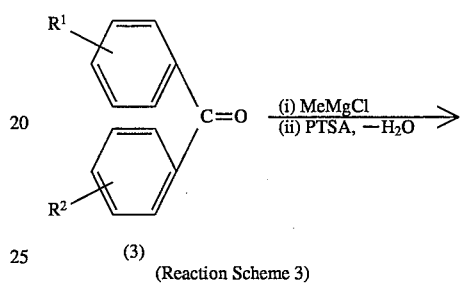

(3)

(Reaction Scheme 3)

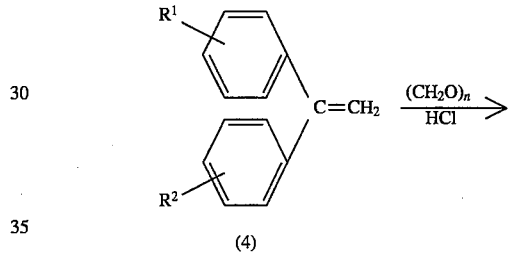

(4)

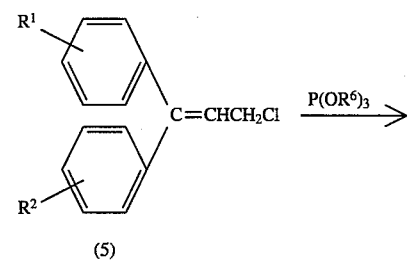

(5)

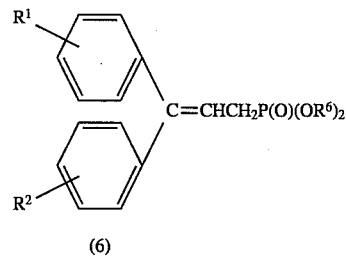

(6)

That is, a 1,1-diarylethylene (4) is first obtained by (i) reacting a benzophenone derivative (3) with methylmagnesium chloride (MeMgCl) and then (ii) dehydrating the resulting alcohol in the presence of an acid. Usable as the acid is one ordinarily used for dehydration reaction, such as, e.g., PTSA (p-toluenesulfonic acid).

The 1,1-diarylethylene (4) can be obtained also by conducting the same reactions (i) and (ii) described above except that an acetophenone derivative (3') is used as a starting compound and a substituted phenylmagnesium bromide is used in place of MeMgCl.

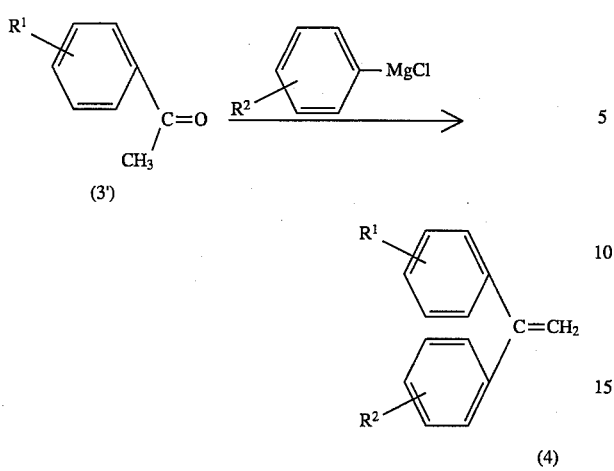

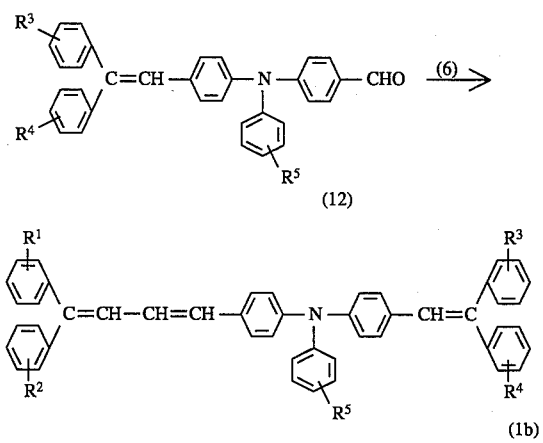

Subsequently, the 1,1-diarylethylene (4) is reacted with paraformaldehyde $(CH_2O)_n$ and hydrogen chloride in acetic acid according to the method described in JP-A-49-75564 to obtain a 3,3-diarylallyl chloride (5).

This 3,3-diarylallyl chloride (5) is reacted with a trialkyl phosphite, whereby the 3,3-diarylallylphosphorous acid dialkyl ester (6) can be obtained.

Examples of the trialkyl phosphite include triethyl phosphite, tripropyl phosphite, and tributyl phosphite.

On the other hand, the triphenylamine derivative of the present invention represented by general formula (1) wherein n=0 (1b) can be synthesized according to reaction scheme 4.

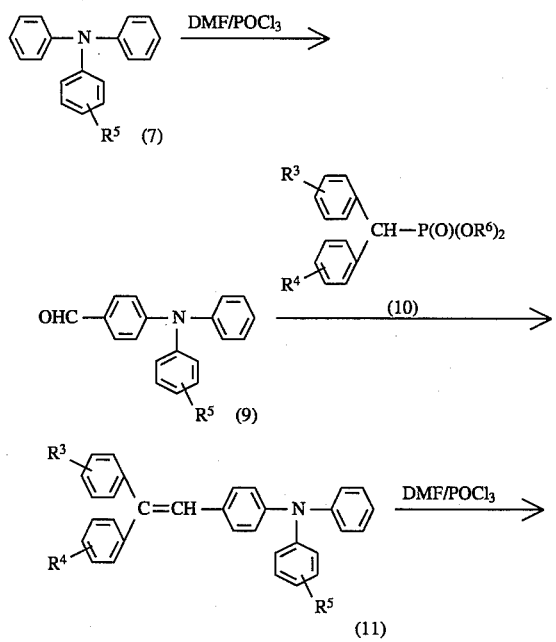

That is, a triphenylamine derivative (7) is reacted with an equimolar amount or slight excess of DMF and an equimolar amount or slight excess of phosphoryl chloride or the like by means of the Vilsmeier-Haack reaction mentioned above, whereby a formyltriphenylamine derivative (9) can be easily obtained. This formyltriphenylamine derivative (9) is then reacted with a diphenylmethylphosphorous acid dialkyl ester derivative represented by general formula (10) in the presence of a base to obtain a diphenylvinyltriphenylamine derivative (11).

The diphenylmethylphosphorous acid dialkyl ester derivative (10) is obtained from corresponding halomethyl compound and trialkyl phosphite by heating the compounds either directly or in a solvent such as, e.g., toluene or xylene.

The diphenylvinyltriphenylamine derivative (11) is subjected to the Vilsmeier-Haack reaction in the same manner as described above to obtain a compound (12). This compound (12) is reacted with a 3,3-diarylallylphosphorous acid dialkyl ester (6), which is obtained as described hereinabove, whereby the desired compound of the invention can be obtained which is the triphenylamine derivative (1b) represented by general formula (1) wherein n=0.

On the other hand, the triphenylamine derivative (1b) represented by general formula (1) wherein n=0 of the present invention can also be synthesized according to the following reaction scheme 5.

(Reaction Scheme 5)

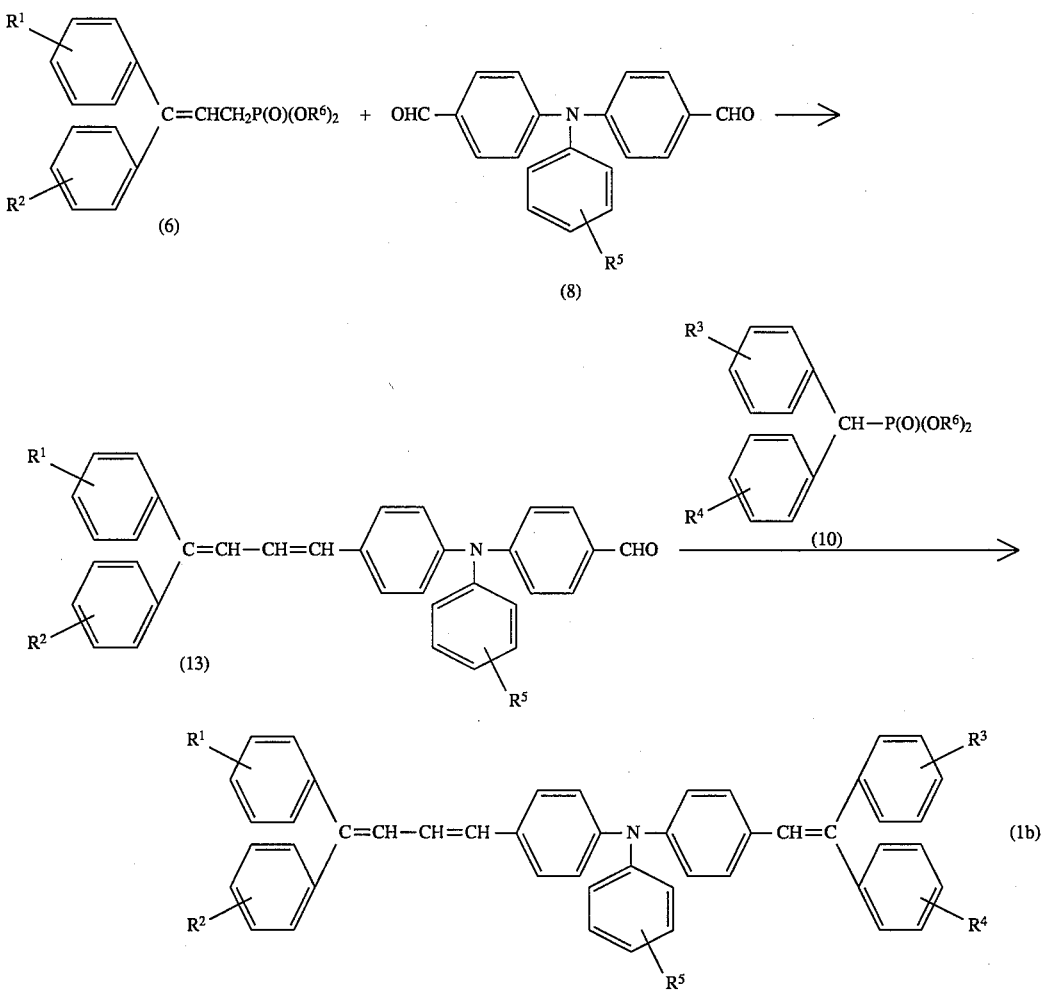

That is, a 3,3-diarylallylphosphorous acid dialkyl ester (6) is reacted with an equimolar amount of a 4,4'-diformyltriphenylamine derivative (8) in the presence of a base to obtain a 4-(4",4"-diphenyl-1",3"-butadienyl)-4'-formyltriphenylamine derivative (13). This compound (13) is reacted with a diphenylmethylphosphorous acid dialkyl ester derivative (10) in the presence of a base to obtain the desired compound of the present invention, i.e., the triphenylamine derivative (1b) represented by general formula (1) wherein n=0.

The triphenylamine derivative (1b) can also be obtained by reacting the compound (8) with the compound (10) and then reacting the obtained product with the compound (6).

The diphenylmethylphosphorous acid dialkyl ester derivative (10) is obtained from corresponding halomethyl compound and trialkyl phosphite by heating the compounds either directly or in a solvent such as, e.g., toluene or xylene.

Further, a triphenylamine derivative (1c) represented by general formula (1) wherein n=1 and $R^1$ and $R^2$ are different from $R^3$ and $R^4$ can be synthesized according to reaction scheme 6.

(Reaction Scheme 6)

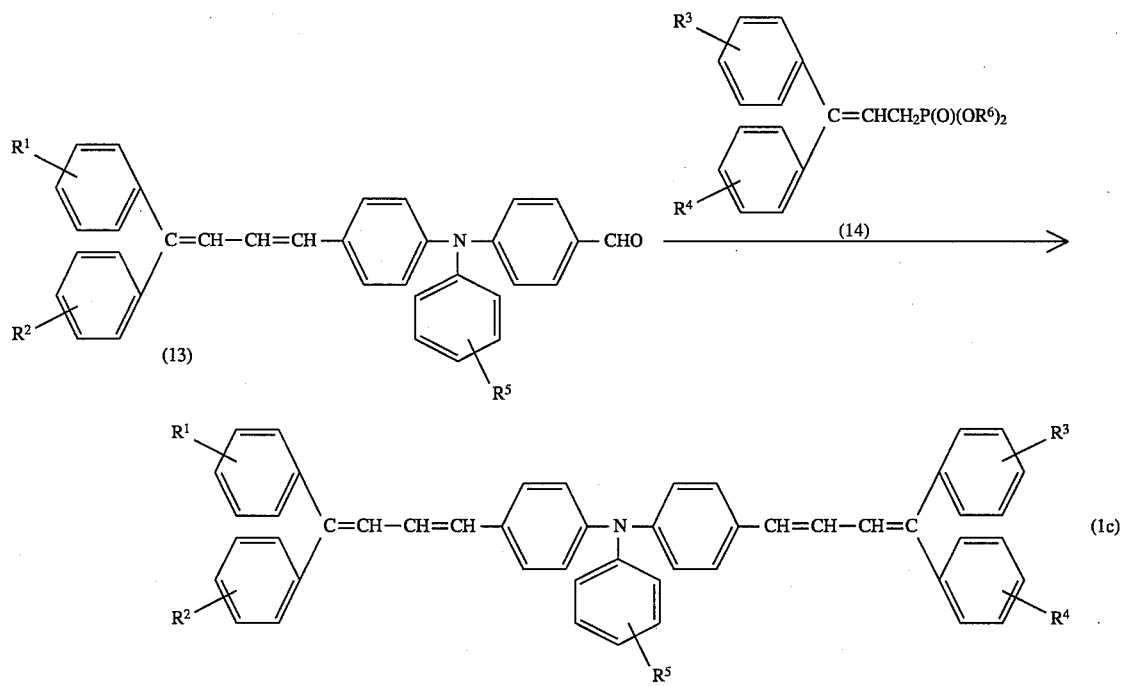

That is, the 4-(4",4"-diphenyl-1",3"-butadienyl)-4'-formyltriphenylamine derivative (13) is reacted with a 3,3-diphenylallylphosphorous acid dialkyl ester (14) which is different from the 3,3-diphenylallylphosphorous acid dialkyl ester (6) in the presence of a base to obtain the desired compound of the present invention, i.e., the triphenylamine derivative (1c) represented by general formula (1) wherein n=1 and $R^1$ and $R^2$ are different from $R^3$ and $R^4$. The 3,3-diphenylallylphosphorous acid dialkyl ester (14) can be synthesized in the same manner as in the synthesis of the 3,3-diphenylallylphosphorous acid dialkyl ester (6).

When the compound (1) of the present invention is used as a charge-transporting material, a high carrier mobility is obtained.

The compound (1) of this invention is also usable in a wide range of fields including organic electroluminescence (EL).

When the compound (1) of this invention is used in an electrophotographic photoreceptor, high sensitivity can be obtained.

The electrophotographic photoreceptor according to the invention specifically comprises a conductive support and, formed thereon, a charge-generating layer and a charge-transporting layer which layers perform their respective functions, the charge-transporting layer comprising the compound (1) of the invention as a charge-transporting material.

The electrophotographic photoreceptor according to the invention may comprise a conductive support and, formed thereon, a monolayer comprising a charge-generating material and the compound (1) of this invention as a charge-transporting material.

The charge-transporting layer comprising the compound (1) of the invention as a charge-transporting material is formed by vapor-depositing the compound (1) as it is on a conductive support or charge-generating layer, or by dissolving the compound (1) into a suitable solvent along with a binder, applying the solution on a conductive support or charge-generating layer, and drying the coating.

On the other hand, the monolayer comprising a charge-generating material and the compound (1) of this invention is obtained by dissolving or dispersing a charge-generating material and the compound (1) into a suitable solvent along with a binder, applying the solution on a conductive support, and drying the coating.

Examples of the binder include polyacrylates, polyamides, acrylic resins, acrylonitrile resins, methacrylic resins, vinyl chloride resins, vinyl acetate resins, phenolic resins, epoxy resins, polyesters, alkyd resins, polycarbonates, polyurethanes, polystyrene, and copolymers thereof. Also usable besides such insulating polymers are organic photoconductive polymers, e.g., polyvinylcarbazole, polyvinylanthracene, and polyvinylene.

Of these binders, the use of polycarbonates is particularly suitable. Suitable polycarbonates are bisphenol A type polycarbonates (for example, Yupilon E series manufactured by Mitsubishi Gas Chemical Company, Inc.), bisphenol Z type polycarbonates (for example, polycarbonate Z series manufactured by Mitsubishi Gas Chemical Company, Inc.), bisphenol A and bisphenol Z disclosed in JP-A-4-179961, and polycarbonates copolymerized with bisphenol A, bisphenol Z and bisphenol carbonates as structural units, for example, bisphenol A/bisphenyl copolycarbonate resin represented by the following formulae:

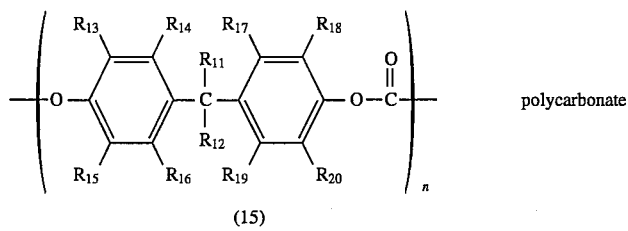

polycarbonate (15)

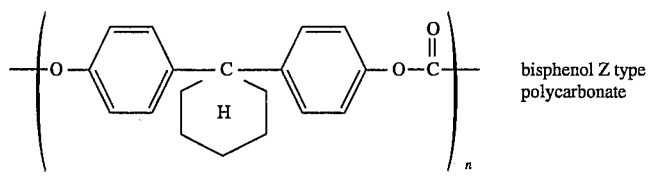

bisphenol Z type polycarbonate (15a)

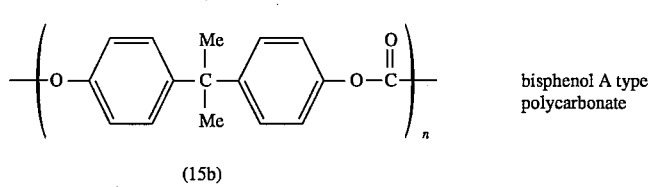

bisphenol A type polycarbonate (15b)

bisphenol copolycarbonate

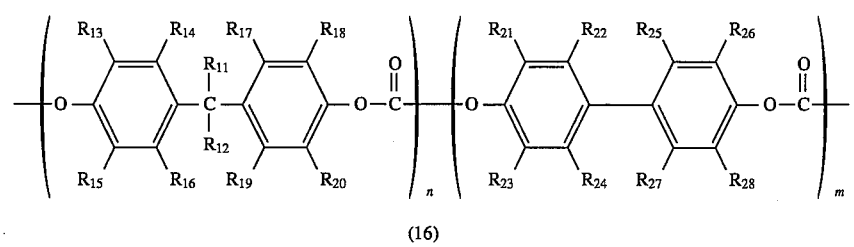

(16)

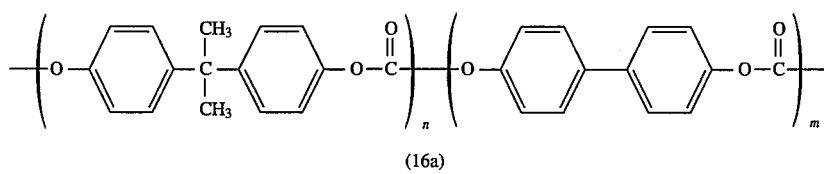

(16a)

(wherein $R_{11}$ and $R_{12}$ each independently represents a hydrogen atom, an alkyl group or an aryl group $R_{11}$ and $R_{12}$ may be taken together to form a ring, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$ and $R_{28}$ each independently represents a hydrogen atom, a halogen atom, an alkyl group or an aryl group, and n and m each represents a molar number of the repeating unit.)

Specific examples of the bisphenol copolycarbonates include, for example, bisphenol A/bisphenol type polycarbonate resin having the following structural formula.

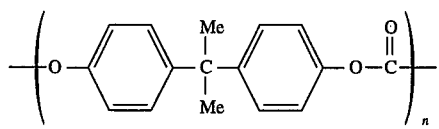

-continued

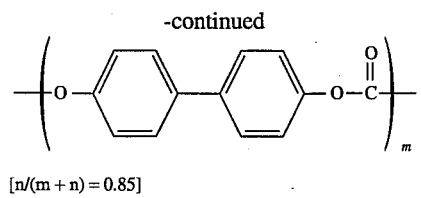

$[n/(m+n) = 0.85]$

Further, polycarbonates having the repeating unit represented by the following structural formula as disclosed in JP-A-6-214412 can be used, in addition to the above-described polycarbonates.

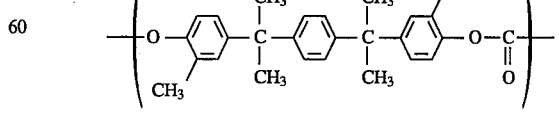

Furthermore, polycarbonates represented by the following structural formula as disclosed in JP-A-6-222581 can be used.

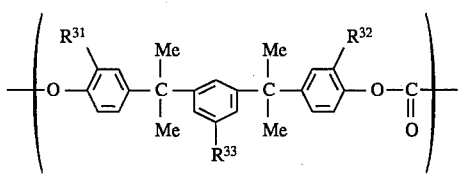

(In formula, $R^{31}$, $R^{32}$ and $R^{33}$ may be the same or different and each represents a hydrogen atom, a halogen atom, an alkyl group, a cycloalkyl group or an arylalkyl group). Specifically, those shown in the following table can be cited, as the above polycarbonates.

| Compound | $R^{31}$ | $R^{32}$ | $R^{33}$ |
|---|---|---|---|
| 1 | H | H | H |
| 2 | H | methyl | H |
| 3 | H | ethyl | H |
| 4 | H | tert-butyl | H |
| 5 | H | phenyl | H |
| 6 | H | benzyl | H |
| 7 | H | dimethylphenylmethyl | H |
| 8 | methyl | H | methyl |
| 9 | methyl | methyl | methyl |
| 10 | methyl | ethyl | methyl |
| 11 | methyl | tert-butyl | methyl |
| 12 | methyl | phenyl | methyl |
| 13 | methyl | benzyl | methyl |
| 14 | methyl | dimethylphenylmethyl | methyl |
| 15 | methyl | cyclohexyl | methyl |
| 16 | Cl | H | Cl |
| 17 | Br | H | Br |
| 18 | isopropyl | H | isopropyl |
| 19 | phenyl | H | phenyl |

The proportion of such a binder to the compound (1) of this invention may be such that the amount of the charge-transporting material is from 10 to 1,000 parts by weight, preferably from 100 to 500 parts by weight, per 100 parts by weight of the binder.

The solvent to be used is not particularly limited, but an organic solvent may be used. Examples thereof include alcohols, e.g., methanol, ethanol, and isopropanol, ketones, e.g., acetone, methyl ethyl ketone, and cyclohexanone, amides, e.g., N,N-dimethylformamide and N,N-dimethylacetamide, sulfoxides, e.g., dimethyl sulfoxide, ethers, e.g., tetrahydrofuran, dioxane, and ethylene glycol dimethyl ether, esters, e.g., ethyl acetate and methyl acetate, halogenated aliphatic hydrocarbons, e.g., methylene chloride, chloroform, 1,2-dichloroethane, dichloroethylene, carbon tetrachloride, and trichloroethylene, and aromatic compounds, e.g., benzene, toluene, xylene, chlorobenzene, and dichlorobenzene.

As the conductive support to be used in the photoreceptor of this invention, a foil or sheet of a metal, e.g., copper, aluminum, silver, iron, zinc, or nickel, or of an alloy thereof may be employed in sheet or drum form. Also usable as the conductive support is one obtained by depositing any of these metals on a plastic film or cylinder or the like by vacuum deposition or electroplating, or one obtained by forming a layer of a conductive compound, e.g., a conductive polymer, indium oxide, or tin oxide, on a support such as glass, paper, or a plastic film by coating or vapor deposition.

The coating may be conducted by using any of such coating techniques as dip coating, spray coating, spinner coating, wire-wound bar coating, blade coating, roller coating, and curtain coating.

In a preferred drying method, the coating is dried first at room temperature and then with heating. It is preferred that the drying with heating be conducted at a temperature of 30° to 200° C. for 5 minutes to 2 hours with or without air blowing.

If desired and necessary, other charge-transporting materials and various additives may be further incorporated into the charge-transporting layer in this invention. Examples of the additives include plasticizers, e.g., biphenyl, m-terphenyl, and dibutyl phthalate, surface lubricants, e.g., silicone oil, graft type silicone polymers, and various fluorocarbons, potential stabilizers, e.g., dicyanovinyl compounds and carbazole derivatives, 1,4-diazabicyclo[2.2.2]octane, monophenol type antioxidants, e.g., 2-tert-butyl-4-methoxyphenol and 2,6-di-tert-butyl-4-methylphenol, bisphenol type antioxidants, amine type antioxidants, and salicylic acid type antioxidants.

The thickness of the charge-transporting layer to be obtained is from 5 to 40 µm, preferably from 10 to 30 µm.

Electrical connection of the thus-obtained charge-transporting layer with a charge-generating layer enables the charge-transporting layer to have the functions of receiving carriers injected from the charge-generating layer in the presence of an electric field and transporting the carriers to the surface of the photosensitive layer.

In this case, the charge-transporting layer may overlie the charge-generating layer or underlie it, but desirably overlies the charge-generating layer.

On the photosensitive layer thus produced, a protective layer may be formed by coating if desired and necessary.

For forming the charge-generating layer, use may be made of one or more materials selected from inorganic charge-generating materials, e.g., selenium, selenium-tellurium, and amorphous silicone, and organic charge-generating materials, e.g., cationic dyes such as pyrylium salt dyes, thiapyrylium salt dyes, azulenium salt dyes, thiacyanine dyes, and quinocyanine dyes, squarylium salt pigments, phthalocyanine pigments, polycyclic quinone pigments such as anthanthrone pigments, dibenzpyrenequinone pigments, and pyranthrone pigments, indigo pigments, quinacridone pigments, azo pigments, and pyrrolopyrrole pigments. These materials may be used alone or in combination to form a layer thereof by vapor deposition or coating.

Of the above-described organic charge-generating substances, those as described in Chem. Rev., 1993, 93, pp. 449–486 are particularly preferred.

Particularly, photocyanine pigments are preferred. Specific examples of thephthalocyanine pigments include oxotitanium phthalocyanine (TiOPc), copper phthalocyanine (CuPc), metal-free phthalocyanine ($H_2Pc$), hydroxygallium phthalocyanine (HOGaPc), vanadyl phthalocyanine (VOPc), and chloroindium phthalocyanine (InClPc). More specifically, α-TiOPc, β-TiOPc, γ-TiOPc, m-TiOPc, Y-TiOPc, A-TiOPc, B-TiOPc, and TiOPc amorphous are cited as the TiOPc and α-$H_2Pc$, β-$H_2Pc$, τ-$H_2Pc$, and X-$H_2Pc$ are cited as the $H_2Pc$.

Azo pigments are also preferred. The azo pigments include monoazo compound, bisazo compound and trisazo compound. Specific examples of the azo compounds are listed below.

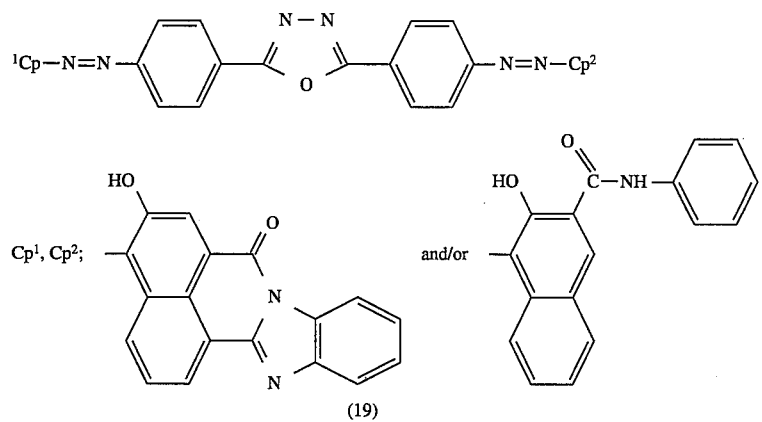
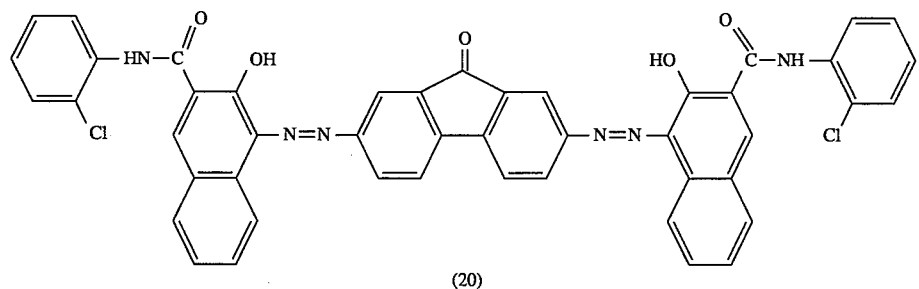
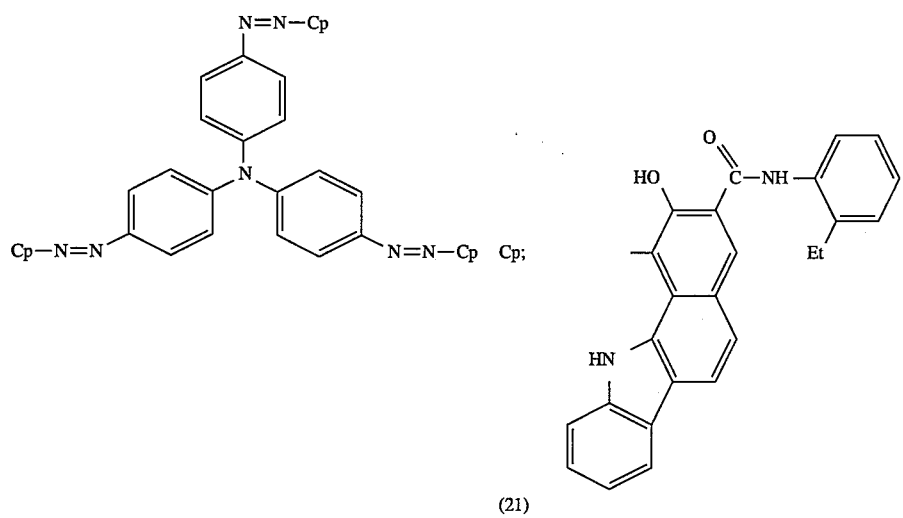
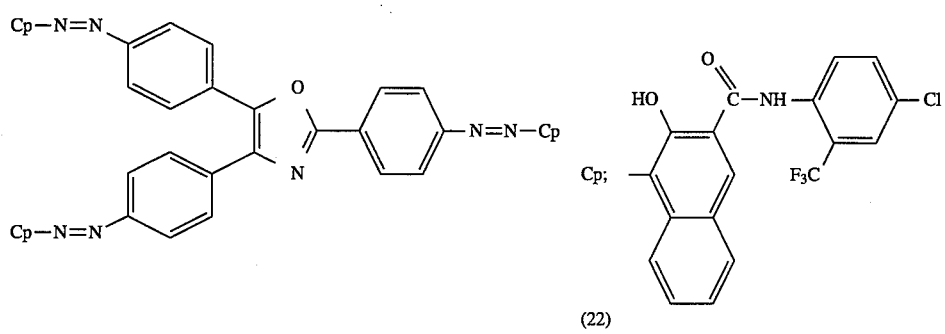

Further, the following perylene compounds or polycyclic quinone compounds are also preferred.

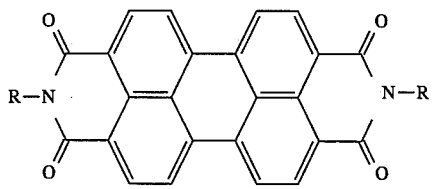

(23)

R = H, lower alkyl or aryl

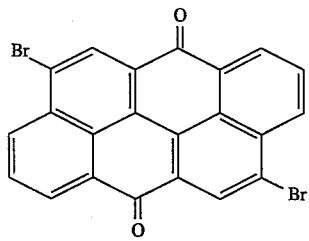

(24)

Besides those materials, any material can be used as long as it generates carriers at a high efficiency upon light absorption.

Thus, an electrophotographic photoreceptor containing a charge-transporting layer comprising the triphenylamine derivative (1) of the present invention can be obtained.

An electrophotographic photoreceptor containing a monolayer comprising a charge-generating material and the compound (1) of this invention as a charge-transporting material, can be also obtained.

As described above, the triphenylamine derivative (1) of this invention, such as those enumerated in Table 1, gives a stable film attaining a high carrier mobility and, when used in forming an electrophotographic photoreceptor, is also excellent in various properties.

The present invention will be explained below in more detail by reference to the following examples, but the invention is not construed as being limited thereto.

In the examples, the analytical instruments and conditions shown below were used.

(1) $^1$H-NMR

Instrument: Type AM-400 (400 MHz), manufactured by Bruker Inc.

Solvent: $CDCl_3$

Internal reference: tetramethylsilane (2) MASS

Instrument: Hitachi M-80B (manufactured by Hitachi Ltd. Japan)

(3) Differential scanning calorimeter (DSC)

Instrument: SSC-5220 (manufactured by Seiko Denshi Kogyo K.K., Japan)

EXAMPLE 1

Synthesis of 4-(4″,4″-Diphenyl-1‴,3‴-butadienyl)-4′-(2‴,2‴-diphenylvinyl)triphenylamine (Exemplified Compound 1; n=0, $R^1, R^2, R^3, R^4, R^5$=H)

(1) Synthesis of 4-Formyltriphenylamine (9a; $R^5$=H)

Into a 1-liter reaction flask were introduced in a nitrogen atmosphere 29.8 g of DMF (dimethylformamide) dried with a molecular sieve and 300 ml of 1,2-dichloroethane Thereto was added dropwise 37.5 g of phosphoryl trichloride with stirring at 5° to 10° C. over a period of 10 minutes. The contents were stirred at room temperature for 1 hour.

Subsequently, a solution of 50 g of triphenylamine in 200 ml of 1,2-dichloroethane was added dropwise at room temperature over a period of 10 minutes. Reaction was thereafter conducted first at room temperature for 18 hours and then with refluxing (86° C.) for 2 hours. The disappearance of the starting materials was ascertained by TLC, before the reaction was terminated.

After cooling, the reaction mixture was poured into 3 liters of ice water, and 1 liter of toluene was added. The mixture was neutralized with soda ash at 60° to 65° C., stirred at that temperature for 1 hour, and then subjected to liquid separation, washing with water, drying with magnesium sulfate, and concentration to obtain 55.78 g of crude crystals. The reaction product was recrystallized twice from isopropyl alcohol, giving 49.9 g of crystals.

Theoretical yield, 89.5% m.p., 138–138.5° C.

(2) Synthesis of 4-(2′,2,-Diphenylvinyl)triphenylamine (11a; $R^3, R^4, R^5$=H)

Into a 1-liter reaction flask were introduced in a nitrogen atmosphere 30 g of the 4-formyltriphenylamine (9a) obtained above, 55.2 g of diethyl diphenylmethylphosphite (10a), and 300 ml of DMF dried with a molecular sieve. The contents were stirred at room temperature to completely dissolve them. Subsequently, 16 g of potassium tert-butoxide was added little by little (the mixture heated from 25 to 50° C.), and reaction was conducted at room temperature for 9 hours. The disappearance of the starting materials was ascertained by TLC, before the reaction was terminated.

After cooling, the reaction mixture was poured into 3 liters of ice water and then subjected to extraction with 500 ml of toluene. The extract was washed with water, dried with magnesium sulfate, and concentrated to obtain 59.37 g of crude crystals. The reaction product was recrystallized from acetonitrile, giving 45.95 g of yellow crystals of 4-(2′,2′-diphenylvinyl)triphenylamine (11a).

Theoretical yield, 98.8% m.p., 87–88° C.

(3) Synthesis of 4-Formyl-4′-(2″,2″-diphenylvinyl)triphenyl amine (12a; $R^3, R^4, R^5$=H)

Into a 1-liter reaction flask were introduced in a nitrogen atmosphere 31.86 g of DMF dried with a molecular sieve and 277 ml of 1,2-dichloroethane. Thereto was added dropwise 33.41 g of phosphoryl trichloride with stirring at 5 to 10° C. over a period of 10 minutes. The contents were then stirred at that temperature for 1 hour.

Subsequently, a solution of 46.16 g of the above-obtained 4-(2′,2′-diphenylvinyl)triphenylamine (11a) in 185 ml of 1,2-dichloroethane was added dropwise at room temperature over a period of 20 minutes. Reaction was thereafter conducted first at room temperature for 17 hours and then with refluxing (86° C.) for 8 hours. The disappearance of the starting materials was ascertained by TLC, before the reaction was terminated.

After cooling, the reaction mixture was poured into 3 liters of ice water, and 1 liter of toluene was added. The mixture was neutralized with soda ash at 60 to 65° C., stirred at that temperature for 1 hour, and then subjected to liquid separation, washing with water (2 liters; twice; pH after washing, 7), drying with magnesium sulfate, and concentration to obtain 49.9 g of a crude product. This product was purified by silica gel column chromatography (eluent: benzene/ethyl acetate=9/1 by volume), giving 43.98 g of 4-formyl-4′-(2″,2″-diphenylvinyl)triphenylamine (12a).

Theoretical yield, 89.4% m.p., 49–50° C.

(4) Synthesis of 4-(4",4"-Diphenyl-1",3"-butadienyl)-4'-(2'",2'"-diphenylvinyl)triphenylamine (Exemplified Compound 1)

Into a 500-ml reaction flask were introduced in a nitrogen atmosphere 3.72 g (8.2 mmol) of the 4-formyl-4'-(2",2"-diphenylvinyl)triphenylamine (12a) obtained above, 3.35 g (9.7 mmol) of diethyl 3,3-diphenylallylphosphite (6a), and 37 ml of DMF dried with a molecular sieve. The contents were stirred at room temperature to completely dissolve them.

Subsequently, 1.09 g (9.7 mmol) of potassium tert-butoxide was added little by little (the mixture heated from 20° to 33° C.), and reaction was conducted at room temperature for 16 hours. The disappearance of the starting materials was ascertained by TLC, before the reaction was terminated.

After cooling, the reaction mixture was poured into 370 ml of methanol, and the resulting precipitate was separated from the liquid by filtration to obtain 5.67 g of crystals. This reaction product was purified by silica gel column chromatography (eluent: benzene/n-hexane=9/1 by volume), giving 4.80 g of a purified reaction product. The purified product was recrystallized from a mixed solvent consisting of 240 ml of acetonitrile and 135 ml of ethyl acetate, giving 2.73 g of yellow crystals of 4-(4",4"-diphenyl-1",3"-butadienyl)-4'-(2'",2'41 -diphenylvinyl)triphenylamine (Exemplified Compound 1) (which had a purity as determined by high-performance liquid chromatography (HPLC) of 99.7%).

Theoretical yield, 52.8% m.p., 108–109° C.

Spectral data for this compound are as follows. $^1$H-NMR spectrum (400 MHz, CDCl$_3$, δ ppm): 6.66 (1H, d, J=15.1 Hz), 6.77 (1H, dd, J=10.7 Hz, 15.1 Hz), 6.80 (1H, d, J=10.7 Hz), 6.87 (2H, d, J=8.7 Hz), 6.90 (1H, s), 6.92 (2H, d, J=8.7 Hz), 7.00–7.05 (3H, m), 7.15 (2H, d, J=8.7 Hz), 7.19–7.42 (22H, m)

MASS (m/e): 627(M$^+$), 451

EXAMPLE 2

Synthesis of 4,4'-Bis(4",4"-diphenyl-1",3"-butadienyl)triphenylamine (Exemplified Compound 2; n=1, $R^1,R^2,R^3, R^4,R^5$=H)

(1) Synthesis of 1,1-Diphenylethylene (4a)

Into a 2-liter reaction flask were introduced in a nitrogen atmosphere 31.6 g (1.3 mol) of magnesium and 50 ml of dry tetrahydrofuran (THF). Slight amounts of iodine and ethyl bromide were further added, following which the initiation of reaction was ascertained.

Thereto was added 600 ml of dry THF with stirring. Methyl chloride gas was then bubbled into the mixture, while the mixture was maintained at 30° to 40° C. by controlling both the amount of the gas being bubbled and cooling. Heat generation ended in 2 hours with the disappearance of the magnesium. The bubbling of methyl chloride gas was then stopped and the mixture was stirred at that temperature for 1 hour to complete the preparation of a Grignard reagent.

To this reaction mixture was added dropwise a liquid mixture of 182.22 g (1.1 mol) of benzophenone (3a; $R^1,R^2$=H) and 364 ml of dry THF at 35° to 40° C. over a period of 30 minutes. This mixture was stirred first at that temperature for 2 hours and then at that temperature for 13 hours to complete the reaction. The resulting solution was added to 1,400 g of cooled 10% aqueous ammonium chloride solution with cooling with ice. The mixture was stirred for 30 minutes, allowed to stand, and then subjected to liquid separation, followed by washing with aqueous common salt solution, drying with magnesium sulfate, and concentration to obtain 200.23 g of crude 1,1-diphenylethanol (theoretical yield based on the benzophenone, 98.6%).

Into a 1-liter reaction flask were introduced 200.23 g of the crude 1,1-diphenylethanol obtained above, 400 ml of toluene, and 1 g of p-toluenesulfonic acid (PTSA). Azeotropic dehydration was conducted for 2 hours with toluene refluxing (94–116° C.). The resulting reaction mixture was cooled, washed with water and then with 2% soda ash solution, dried with magnesium sulfate, and concentrated to obtain 190.09 g of crude 1,1-diphenylethylene (4a; $R^1,R^2$= H). This crude 1,1-diphenylethylene (4a) was distilled with a Claisen flask equipped with a vigreux (b.p., 103° C./1 mmHg), giving 174.06 g of 1,1-diphenylethylene (4a). The theoretical yield based on the benzophenone was 96.5%.

(2) Synthesis of 3,3-Diphenylallyl Chloride (5a; $R^1,R^2$=H)

Into a 300-ml reaction flask were introduced 54.13 g (0.3 mol) of the 1,1-diphenylethylene (4a) obtained above, 108.26 g of acetic acid, and 13.51 g (0.45 mol) of paraformaldehyde. Hydrogen chloride in an amount of 13.67 g (0.375 mol) was then bubbled into the mixture with stirring at 30° C. over a period of 3.5 hours, while the reaction mixture was kept being cooled at 30° C. because slight heat generation occurred.

After the bubbling of hydrogen chloride was stopped, the reaction mixture was stirred at that temperature for 2 hours and then allowed to stand overnight. The resulting reaction mixture was poured into 200 ml of water and extracted with 200 ml of toluene. The extract was washed with water, with 2% soda ash solution, and then with water, dried with magnesium sulfate, and concentrated to obtain 68.42 g of a crude reaction product. This crude product was distilled with a Claisen flask equipped with a vigreux (b.p., 120°–132° C./1 mmHg), giving 57.51 g of 3,3-diphenylallyl chloride (5a).

Theoretical yield based on (3a), 79%

$^1$H-NMR spectrum (400 MHz, CDCl$_3$, δ ppm): 4.11 (2H, d, J=8.0 Hz), 6.23 (1H, t, J=8.0 Hz), 7.21–7.41 (10H, m)

MASS (m/e): 228(M$^+$), 193, 178, 115

(3) Synthesis of Diethyl 3,3-diphenylallylphosphite (6a; $R^1,R^2$=H)

A mixture of 40.75 g (0.155 mol) of 3,3-diphenylallyl chloride (5a) and 94.48 g (0.569 mol) of triethyl phosphite was stirred with refluxing for 24 hours. The disappearance of the 3,3-diphenylallyl chloride (5a) was ascertained by gas chromatography (GC), before the reaction was terminated. After cooling, the reaction mixture was distilled with a Claisen flask equipped with a vigreux (b.p.,170°–203° C./1 mmHg), giving 55.39 g of diethyl 3,3-diphenylallylphosphite (6a).

Theoretical yield, 99%

$^1$H-NMR spectrum (400 MHz, CDCl$_3$, δ ppm): 1.31 (6H, t, J=7.0 Hz), 2.71 (2H, dd, J=7.9 Hz, J=22.4 Hz), 4.08 (6H, dt, J=7.1 Hz, J=7.6 Hz), 6.12 (1H, q, J=7.9 Hz, J=7.6 Hz), 7.22–7.38 (10H, m)

MASS (m/e): 330(M$^+$), 193, 115

(4) Synthesis of 4,4'-Diformyltriphenylamine (8a; $R^3$=H)

Into a 1-liter reaction flask were introduced 44.74 g (0.612 mol) of dimethylformamide (DMF) and 200 ml of dichloroethane. Thereto was added dropwise 93.82 g (0.612 mol) of phosphoryl trichloride at 5° to 10° C. over a period of 30 minutes.

A solution of 50 g (0.204 mol) of triphenylamine (7a) in 200 ml of dichloroethane was then added gradually at room temperature over a period of 30 minutes. The resulting mixture was stirred first at room temperature for 12 hours and then with refluxing for 24 hours.

After cooling, 44.74 g (0.612 mol) of DMF and 93.82 g (0.612 mol) of phosphoryl trichloride were added, and the mixture was stirred with refluxing for 24 hours. This procedure was repeated three times. The reaction mixture was then poured into 4 liters of ice water, and 1 liter of toluene was added. The resulting mixture was neutralized with sodium carbonate, stirred at 65° C. for 1 hour, and then subjected to liquid separation, washing with water, drying, and concentration to obtain 56.6 g of a crude reaction product. This reaction product was recrystallized twice from isopropyl alcohol, giving 24.3 g of 4,4'-diformyltriphenylamine (8a) (theoretical yield, 39.5%).

m.p., 148.5°–149.5° C.

(5) Synthesis of 4,4'-Bis(4'',4''diphenyl-1'',3''-butadienyl)triphenylamine (Exemplified Compound 2)

Into a 100-ml reaction flask were introduced 3.0 g (9.93 mmol) of 4,4'-diformyltriphenylamine (8a), 7.52 g (21.83 mmol) of diethyl 3,3-diphenylallylphosphite (6a), and 60 ml of DMF. Thereto was added 2.67 g (23.8 mmol) of potassium tert-butoxide little by little. The resulting mixture was stirred for 17 hours. The disappearance of the 4,4'-diformyltriphenylamine (8a) was ascertained by TLC (thin-layer chromatography), before the reaction was terminated.

This reaction mixture was poured into 600 ml of methanol, and the resulting precipitate was separated from the liquid by filtration and washed with methanol to obtain 5.8 g of crude crystals. The reaction product was recrystallized from toluene, giving 3.31 g of 4,4'-bis(4'',4''-diphenyl-1'',3''-butadienyl)triphenylamine (Exemplified Compound 2) (theoretical yield, 50.9%).

m.p., 115°–116° C.

Spectral data for this compound are as follows.

$^1$H-NMR spectrum (400 MHz, CDCl$_3$, δ ppm): 6.67 (2H, d, J=15.0 Hz), 6.78 (2H, dd, J=15.0, 10.7 Hz), 6.85 (2H, d, J=10.7 Hz), 6.93–7.40 (33H, m)

In addition, minor peaks of 6.25 (t, J=11 Hz) and 6.36 (d, J=11.6 Hz) were observed (cis-double bond).

MASS (m/e): 653(M$^+$), 477, 373, 281

EXAMPLE 3

Synthesis of 4,4'-Bis[4'',4''-di(p-tolyl)-1'',3''-butadienyl]triphenylamine (Exemplified Compound 5; n=1, R$^1$,R$^2$,R$^3$, R$^4$=4-Me, R$^5$=H)

(1) Synthesis of 1,1-Di(p-tolyl)ethylene (4b; R$^1$,R$^2$=4-Me)

Into a 1-liter reaction flask were introduced in a nitrogen atmosphere 15.6 g (0.65 mol) of magnesium and 20 ml of THF. Slight amounts of ethyl iodide and iodine were added thereto to initiate reaction. A solution of 111.15 g (0.65 mol) of p-bromotoluene in 500 ml of THF was then added dropwise at room temperature to 40° C. over a period of 2 hours to prepare a Grignard reagent.

Thereto was added dropwise a solution of 83.75 g (0.625 mol) of p-methylacetophenone in 200 ml of THF at that temperature over a period of 3 hours. After the addition, the mixture was stirred first at room temperature for 3 hours and then with refluxing for 4 hours. Theresuiting reaction mixture was cooled and poured into 1 liter of 5% aqueous sulfuric acid solution to conduct hydrolysis.

This solution was extracted with toluene, and the extract was washed with aqueous soda ash solution and then with water and concentrated. Thereto were added 300 ml of toluene and 0.5 g of PTSA. The resulting mixture was stirred with refluxing for 4 hours to conduct azeotropic dehydration, followed by washing with aqueous-soda ash solution, washing with water, and concentration.

The resulting crude reaction product was distilled with a Claisen flask equipped with a vigreux (b.p., 120°–121° C./1 mmHg), giving 98.5 g of 1,1-di(p-tolyl)ethylene (4b). Theoretical yield based on the p-methylacetophenone, 75.8% (2) Synthesis of 3,3-Di(p-tolyl)allyl Chloride (5b; R$^1$,R$^2$=4-Me)

Synthesis was conducted in the same manner as in (2) in Example 2 except that 70.5 g (0.337 mol) of 1,1-di(p-tolyl)ethylene (4b) was used in place of 1,1-diphenylethylene (4a) and that paraformaldehyde was used in an amount of 15.1 (0.505 mol). Thus, 58.7 g of a reaction product was obtained (b.p., 153°–173° C./1 mmHg; theoretical yield, 67.9%).

This reaction product was recrystallized from hexane, giving 49.0 g of 3,3-di(p-tolyl)allyl chloride (5b).

Theoretical yield, 56.7% m.p., 66° C.

Spectral data for the 3,3-di(p-tolyl)allyl chloride (5b) are as follows.

$^1$H-NMR spectrum (400 MHz, CDCl$_3$, δ ppm): 2.33 (3H, s), 2.39 (3H, s), 4.13 (2H, d, J=8.1 Hz), 6.17 (1H, t, J=8.1 Hz), 7.01–7.24 (8H, m)

MASS (m/e): 256(M$^+$), 221, 206,165, 129

(3) Synthesis of Diethyl 3,3-Di-p-tolylallylphosphite (6b; R$^1$,R$^2$=4-Me)

Reactions were conducted in the same manner as in (3) in Example 2 except that 35.0 g (0.1365 mol) of 3,3-di(p-tolyl)allyl chloride (5b) was used in place of 3,3-diphenylallyl chloride (5a) and that triethyl phosphite was used in an amount of 68 g (0.409 mol). As a result, 49.3 g of a distillation residue was obtained. This residue was recrystallized from hexane, giving 29.9 g of diethyl 3,3-di (p-tolyl)allylphosphite (6b).

Theoretical yield, 61.16% m.p., 56.0° C.

Spectral data for this compound are as follows.

$^1$H-NMR spectrum (400 MHz, CDCl$_3$, δ ppm): 1.30 (6H, t, J=7.1 Hz), 2.32 (3H, s), 2.39 (3H, s), 2.71 (2H, dd, J=7.9 Hz, J=22.4 Hz), 4.07 (4H, q, J=7.1 Hz, J=8.1 Hz), 6.05 (1H, dd, J=7.9 Hz, J=15.2 Hz), 7.06–7.19 (8H, m)

MASS (m/e): 358(M$^+$), 221, 129

(4) Synthesis of 4,4'-Bis[4'',4''-di(p-tolyl)-1'',3''-butadienyl]triphenylamine (Exemplified Compound 5)

Reactions were conducted in the same manner as in (5) in Example 2 except that 4,4'-diformyltriphenylamine (8a) was used in an amount of 3.01 g (10 mmol) and that 7.52 g (21 mmol) of diethyl 3,3-di(p-tolyl)allylphosphite (6b) was used in place of diethyl 3,3-diphenylallylphosphite (6a). Thus, 3.51 g of 4,4'-bis[4'',4''-di(p-tolyl)-1'',3''-butadienyl]triphenylamine (Exemplified Compound 5) was obtained. Theoretical yield, 49.4%; m.p., 123°–124° C.

$^1$H-NMR spectrum (400 MHz, CDCl$_3$, δ ppm): 2.34 (6H, s), 2.40 (6H, s), 6.62–6.67 (2H, m), 6.78–6.82 (4H, m), 6.93–7.29 (29H, m)

In addition, minor peaks of 6.24 (t, J=11.4 Hz) and 6.35 (d, J=11.4 Hz) were observed (cis-double bond).

MASS (m/e): 709(M$^+$), 490, 219,169

EXAMPLE 4

Synthesis of 4-Methyl-4',4''-bis[4''',4'''-di(p-tolyl)-1''',3'''-butadienyl]triphenylamine (Exemplified Compound 13, n=1, R$^1$,R$^2$,R$^3$,R$^4$,R$^5$=4-Me)

(1) Synthesis of 4,4'-Diformyl-4''-methyltriphenylamine (8b)

Synthesis was conducted in the same manner as in (4) in Example 2 except that 28.73 g (0.111 mol) of 4-methyltriphenylamine (7b) was used in place of triphenylamine (7a). Thus, 3.84 g of 4,4'-diformyl-4''-methyltriphenylamine (8b) was obtained.

Theoretical yield, 11.8% m.p., 153.5–154° C.

(2) Synthesis of 4-Methyl-4',4"-bis[4'",4'"-di(p-tolyl)-1'", 3'"-butadienyl]butadienyl]triphenylamine (Exemplified Compound 13)

Reactions were conducted in the same manner as in (5) in Example 2 except that 1.0 g (3.2 mmol) of 4,4'-diformyl-4"-methyltriphenylamine (8b) was used in place of 4,4'-diformyltriphenylamine (8a) and that 3.43 g (9.5 mmol) of diethyl 3,3-di(p-tolyl)allylphosphite (6b) was used in place of diethyl 3,3-diphenylallylphosphite (6a). Thus, 1.55 g of 4-methyl-4',4"-bis[4'",4'"-di(p-tolyl)-1'",3'"-butadienyl] triphenylamine (Exemplified Compound 13) was obtained.

Theoretical yield, 67.2% m.p., 134°–135° C.

Spectral data for this compound are as follows.

$^1$H-NMR spectrum (400 MHz, CDCl$_3$, δ ppm): 2.29 (3H, s), 2.33 (6H, s), 2.39 (6H, s), 6.64 (2H, dd, J=14.5 Hz, J=6.7 Hz), 6.75–6.82 (4H, m), 6.91–7.20 (28H, m)

In addition, minor peaks of 6.23 (t, J=11.4 Hz) and 6.32 (d, J=11.4 Hz) were observed (cis-double bond).

MASS (m/e): 723(M$^+$), 504

EXAMPLE 5

Synthesis of 4-Methoxy-4',4"-bis[4'",4'"-di(p-tolyl)-1'"3'"-butadienyl]triphenylamine (Exemplified Compound 18; n=1, $R^1,R^2,R^3,R^4$=4-Me, $R^5$=4-MeO)

(1) Synthesis of 4,4'-Diformyl-4"-methoxytriphenylamine (8c)

Reactions were conducted in the same manner as in (4) in Example 2 except that 20.0 g (0.075 mol) of 4-methoxytriphenylamine (7c) was used in place of triphenylamine (7a). Thus, 19.0 g of 4,4'-diformyl-4"-methoxytriphenylamine (8c) was obtained.

Theoretical yield, 76.5%; m.p., 113°–114° C.

Spectral data for this compound are as follows.

$^1$H-NMR spectrum (400 MHz, CDCl$_3$, δ ppm): 3.85 (3H, s), 6.94 (2H, d, J=9.0 Hz), 7.12 (2H, d, J=9.0 Hz), 7.17 (4H, d, J=8.7 Hz), 7.56 (4H, d, J=8.7 Hz), 9.88 (2H, s)

MASS (m/e): 331(M$^+$), 316, 259,230

(2) Synthesis of 4-Methoxy-4',4"-bis[4'",4'"-di(p-tolyl)-1'", 3'"-butadienyl]triphenylamine (Exemplified Compound 18)

Reactions were conducted in the same manner as in (5) in Example 2 except that 3.58 g (10 mmol) of diethyl 3,3-di(p-tolyl)allylphosphite (6b) was used in place of diethyl 3,3-diphenylallylphosphite (6a) and that 1.655 g (5.0 mmol) of 4,4'-diformyl-4"-methoxytriphenylamine (8c) was used in place of 4,4'-diformyltriphenylamine (8a). Thus, 1.19 g of 4-methoxy-4',4"-bis[4'",4'"-di(p-tolyl)-1'",3'"-butadienyl] triphenylamine (Exemplified Compound 18) was obtained.

Theoretical yield, 76.5%; m.p., 127.5°–128.5° C.

Spectral data for this compound are as follows.

$^1$H-NMR spectrum (400 MHz, CDCl$_3$, δ-ppm): 2.34 (6H, s), 2.40 (6H, s), 3.79 (3H, s), 6.23 (2H, d, J=14.9 Hz),. 6.79–6.83 (6H, m), 6.90 (4H, d, J=7.4 Hz), 7.03 (2H, d, J=8.6 Hz), 7.08–7.21 (20H, m)

MASS (m/e): 739(M$^+$), 601, 92

EXAMPLE 6

Synthesis of Exemplified Compound 27 (in general formula 1, $R^1=R^2=R^3=R^4$=4-Me, $R^5$=4-Br, n=1)

(1) Synthesis of 4,4'-Diformyl-4"-bromotriphenylamine (8d; $R^5$=4-Br)

In the same manner as in the synthesis of 4,4'-diformyltriphenylamine (8a), 2.92 g of 4,4'-diformyl-4"-bromotriphenylamine (8d) was obtained from 12.0 g (0.037 mol) of 4-bromotriphenylamine (7d).

m.p., 205°–206° C.; Theoretical yield, 20.8%

Spectral data for this compound are as follows.

Mass spectrum; m/e 379(M$^+$), 271

$^1$H-NMR spectrum (400 MHz, δ; ppm in CDCl$_3$): 7.06 (2H, d, J=8.8 Hz), 7.19 (4H, d, J=8.8 Hz), 7.50 (2H, d, J=8.8 Hz), 7.79 (4H, d, J=8.8 Hz), 9.91 (2H, s)

(2) Synthesis of Exemplified Compound 27

From 1.79 g (5 mmol) of diethyl 3,3-di-p-triallylphosphite (6b) and 0.76 g (2 mmol) of 4,4'-diformyl-4"-bromotriphenylamine (8d), 1.35 g of Exemplified Compound 27 was obtained in the same manner as that for Exemplified Compound 2.

Theoretical yield, 85.6%; m.p., 146°–149° C.

Spectral data for the Exemplified Compound 27 are as follows.

Mass spectrum (SIMS); m/e 789(M$^+$+1), 570

$^1$H-NMR spectrum (400 MHz, δ; ppm in CDCl$_3$): 2.34 (6H, s), 2.41 (6H, s), 6.61–6.65 (2H, m), 6.78–6.82 (4H, m), 7.08–7.32 (28H, m)

In addition, minor peaks of 6.20 to 6.35 (m) were observed (cis-double bond).

SYNTHESIS EXAMPLE 1

Synthesis of 4-(4',4'-Diphenylbutadienyl)triphenylamine (Comparative Compound 1)

Into a 100-ml reaction flask were introduced 3.76 g (13.7 mmol) of triphenylamine monoaldehyde (9a), 5.44 g (16.4 mmol) of diethyl 3,3-diphenylallylphosphite, and 38 ml of dry DMF. The contents were stirred to completely dissolve them. Thereto was added 1.84 g (16.4 mmol) of potassium t-butoxide little by little. This mixture was stirred at room temperature for 16 hours. The disappearance of the starting materials was ascertained by TLC, before the reaction was terminated. The resulting reaction mixture was extracted with benzene, and the extract was concentrated to obtain 7.24 g of a concentrate. This concentrate was purified by silica gel column chromatography (eluent: benzene) to obtain 6.09 g of a reaction product, which was then recrystallized from an ethyl acetate/hexane mixed solvent, giving 4.03 g of 4-(4',4'-diphenylbutadienyl)triphenylamine (Comparative Compound 1). Th, 65.2%; m.p., 148.5°14 149° C.

Spectral data for this compound are as follows.

Mass spectrum; m/e 449(M$^+$), 258, 203, 168

$^1$H-NMR spectrum (400 MHz, δ; ppm in CDCl$_3$): 6.67 (1H, d, J=15.1 Hz), 6.78 (1H, dd, J=10.7 Hz, 15.1 Hz), 6.89 (1H, d, J=10.7 Hz), 6.94 (2H, d, J=8.7 Hz), 7.00 (2H, d, J=7.3 Hz), 7.06 (4H, d, J=7.5 Hz),. 7.16 (2H, d, J=8.7 Hz), 7.20–7.41 (14H, m)

SYNTHESIS EXAMPLE 2

Synthesis of 4,4'-Bis(diphenylvinyl)triphenylamine (Comparative Compound 2)

From 1.51 g (5.02 mmol) of 4,4'-diformyltriphenylamine (8a) and 3.46 g (11.4 mmol) of diethyl diphenylmethylphosphite, 2.53 g of 4,4'-bis(diphenylvinyl)triphenylamine was obtained in accordance with JP-A-60-174749.

Th, 83.9%; m.p., 156°–157° C.

SYNTHESIS EXAMPLE 3

Synthesis of 1,1-Diphenyl-4-(p-dimethylaminophenyl)-1, 3-butadiene (Comparative Compound 3)

In 50 ml of dry DMF were dissolved 3.3 g of diethyl 3,3-diphenylallylphosphite (6a) and 1.49 g of p-dimethylaminobenzaldehyde. Thereto was added 1.2 g of potassium t-butoxide little by little. The reactants were allowed to react at room temperature.

After cooling, the reaction mixture was poured into methanol, and the resulting crystals were separated by filtration and recrystallized from ethyl acetate to obtain 2.35 g of 1,1-diphenyl-4-(p-dimethylaminophenyl)-1,3-butadiene (Comparative Compound 3).

Yield, 72.3%; m.p., 179°–180° C.

SYNTHESIS EXAMPLE 4

Synthesis of 1,1-Diphenyl-4-(p-di-n-propylaminophenyl)-1,3-butadiene (Comparative Compound 4)

The same procedures as in Synthesis Example 3 were conducted except that 2.05 g of p-di-n-propylaminobenzaldehyde was used in place of 1.49 g of p-dimethylaminobenzaldehyde. Thus, 2.35 g of 1,1-diphenyl-4-(p-di-n-propylaminophenyl)-1,3-butadiene (Comparative Compound 4) was obtained.

Yield, 73.8%; m.p., 94.5°–95.2° C.

APPLICATION EXAMPLES 1 TO 4

One part by weight of chlorodian blue (CDB) and 1 part by weight of a polycarbonate resin (Yupilon E-2000, manufactured by Mitsubishi Gas Chemical Company, Inc., Japan) were kneaded in a ball mill for 5 hours along with 30 parts by weight of dichloroethane as a solvent. The pigment dispersion obtained was applied with a wire-wound bar on a sheet obtained by vapor-depositing aluminum on a poly(ethylene terephthalate) (PET) film, and the coating was dried at 45° C. for 3 hours to form a charge-generating layer having a thickness of about 1 μm. Further, 1 part by weight of each of the Exemplified Compounds 2, 5, 13, and 18 synthesized in Examples 2 to 5 and 1 part by weight of a polycarbonate resin (Polycarbonate Z, manufactured by Mitsubishi Gas Chemical Company, Inc.) were mixed in 8 parts by weight of dichloroethane to dissolve them. Each of these solutions was applied on the charge-generating layer with a doctor blade and dried at 80° C. for 3 hours. Thus, photoreceptors 1 to 4 were produced.

The electrophotographic photoreceptors thus obtained were statically examined for electrophotographic properties with an electrostatic recording tester Type SP-428 (manufactured by Kawaguchi Denki Seisakusho, Japan). In this test, the photoreceptor was electrostatically charged by 5-second corona discharge at −6 kV to measure the resulting surface potential $V_0$ (unit: −V), and the resulting photoreceptor was placed in the dark for 5 seconds and then irradiated with light from a tungsten lamp at an illuminance of 5 lx to determine the exposure dose required for the surface potential to decrease by half, i.e., half-decay exposure $E_{1/2}$ (lux.sec), and the residual surface potential $V_{R10}$ (−V) after 10-second irradiation at an illuminance of 5 lx. The results obtained are summarized in Table 2.

COMPARATIVE EXAMPLES 1 AND 2

Photoreceptors 5 and 6 were produced and examined for electrophotographic properties in the same manner as in Application Examples 1 to 4 except that Comparative Compounds 1 and 2 synthesized in Synthesis Examples 1 and 2 were used in place of Exemplified Compounds 2, 5, 13, and 18. The results obtained are summarized in Table 2.

A comparison between Application Examples 1 to 4 and Comparative Examples 1 and 2 clearly shows that the photoreceptors 1 to 4 employing compounds of this invention each has a small half-decay exposure ($E_{1/2}$) and high sensitivity, thus demonstrating that the compounds of this invention are effective as an electrophotographic photoreceptor material.

APPLICATION EXAMPLES 5 TO 8

On a thin aluminum film formed on a polyester film by vapor deposition, oxotitanium phthalocyanine (TiOPc) was vacuum-deposited at $10^{-6}$ Torr to a thickness of about 0.8 μm to form a charge-generating layer. Further, 1 part by weight of each of the Exemplified Compounds 1, 2, 13, and 18 synthesized in Examples 1, 2, 4, and 5 and 1 part by weight of a polycarbonate resin (Polycarbonate Z, manufactured by Mitsubishi Gas Chemical Company, Inc.) were mixed in 8 parts by weight of dichloroethane to dissolve them. Each of these solutions was applied on the charge-generating layer with a doctor blade and dried at 80° C. for 3 hours. Thus, photoreceptors 7 to 10 were produced. Their electrophotographic properties were examined in the same manner as in Application Examples 1 to 4. The results obtained are summarized in Table 2.

COMPARATIVE EXAMPLES 3 TO 5

Photoreceptors 11, 12, and 13 were produced and examined for electrophotographic properties in the same manner as in Application Examples 5 to 8 except that Comparative Compounds 2, 3, and 4 synthesized in Synthesis Examples 2 to 4 were used in place of Exemplified Compounds 1, 2, 13, and 18. The results obtained are summarized in Table 2.

The photoreceptors 7 to 10, although equal in half-decay exposure ($E_{1/2}$) to the photoreceptors 11 and 12, have higher potentials after charging than the photoreceptors 11 and 12, showing that they are excellent in the ability to be electrostatically charged. Further, the photoreceptors 7 to 10 have higher sensitivity and lower residual potentials than the photoreceptor 13. That is, the results clearly show that the compounds of this invention each is an excellent electrophotographic photoreceptor material.

APPLICATION EXAMPLES 9 TO 13

One part by weight of τ-form metal-free phthalocyanine (τ-$H_2$Pc) and 1 part by weight of a butyral resin (Poly(vinyl butyral) BM-1, manufactured by Sekisui Chemical Co., Ltd., Japan) were kneaded in a ball mill for 5 hours along with 30 parts by weight of tetrahydrofuran as a solvent. The pigment dispersion obtained was applied on a sheet obtained by vapor-depositing aluminum on a poly(ethylene terephthalate) (PET) film, and the coating was dried at 50° C. for 2 hours. Further, 1 part by weight of each of Exemplified Compounds 2, 5, 13, 18, and 27 synthesized in Examples 2 to 6 and 1 part by weight of a polycarbonate resin (Polycarbonate Z, manufactured by Mitsubishi Gas Chemical Company, Inc.) were mixed in 8 parts by weight of dichloroethane to dissolve them. Each of these solutions was applied on the charge-generating layer with a doctor blade and dried at 80° C. for 2 hours to prepare photoreceptors 14 to 18. The photoreceptors thus obtained were examined for electrophotographic properties in the same manner as in Application Examples 1 to 4. The results obtained are summarized in Table 3.

COMPARATIVE EXAMPLE 6

A photoreceptor 19 was produced in the same manner as in Application Examples 9 to 13 except that Comparative Compound 4 synthesized in Synthesis Example 4 was used in place of Exemplified Compounds 2, 5, 13, 18, and 27. Its electrophotographic properties were examined in the same manner as in Application Examples 1 to 4. The results obtained are shown in Table 3.

The photoreceptors 14 to 18 exhibit excellent electrophotographic properties. That is, they have significantly higher potentials after charging than the photoreceptor 19 and are low in residual potential despite their high sensitivity. The results demonstrate that the compounds of this invention are extremely effective as an electrophotographic photoreceptor material.

APPLICATION EXAMPLES 14 TO 18

One part by weight of x-form metal-free phthalocyanine (x-$H_2$Pc) and 1 part by weight of a butyral resin (Poly(vinyl butyral) BM-1, manufactured by Sekisui Chemical Co., Ltd.) were kneaded in a ball mill for 5 hours along with 30 parts by weight of tetrahydrofuran as a solvent. The pigment dispersion obtained was applied on a sheet obtained by vapor-depositing aluminum on a poly(ethylene terephthalate) (PET) film, and the coating was dried at 50° C. for 2 hours. Further, 1 part by weight of each of Exemplified Compounds 1, 2, 13, 18, and 27 synthesized in Examples 1 to 6 and 1 part by weight of a polycarbonate resin (Polycarbonate Z, manufactured by Mitsubishi Gas Chemical Company, Inc.) were mixed in 8 parts by weight of dichloroethane to dissolve them. Each of these solutions was applied on the charge-generating layer with a doctor blade and dried at 80° C. for 2 hours to prepare photoreceptors 20 to 24. The photoreceptors thus obtained were examined for electrophotographic properties in the same manner as in Application Examples 1 to 4. The results obtained are summarized in Table 3.

TABLE 2

|  | Photoreceptor No. | Charge-generating material | Charge-transporting material | $V_0$ (–V) | $V_{R10}$ (–V) | $E_{1/2}$ (lux · sec) |
| --- | --- | --- | --- | --- | --- | --- |
| Application Example 1 | 1 | CDB | Exemplified Compound 2 | 900 | 0 | 3.1 |
| Application Example 2 | 2 | " | Exemplified Compound 5 | 500 | 0 | 3.0 |
| Application Example 3 | 3 | " | Exemplified Compound 13 | 670 | 0 | 2.7 |
| Application Example 4 | 4 | " | Exemplified Compound 18 | 620 | 0 | 2.3 |
| Comparative Example 1 | 5 | " | Comparative Compound 1 | 820 | 2 | 6.8 |
| Comparative Example 2 | 6 | " | Comparative Compound 2 | 380 | 0 | 5.9 |
| Application Example 5 | 7 | vapor-deposited TiOPc | Exemplified Compound 1 | 660 | 20 | 0.8 |
| Application Example 6 | 8 | vapor-deposited TiOPc | Exemplified Compound 2 | 700 | 0 | 0.5 |
| Application Example 7 | 9 | vapor-deposited TiOPc | Exemplified Compound 13 | 540 | 0 | 0.8 |
| Application Example 8 | 10 | vapor-deposited TiOPc | Exemplified Compound 18 | 470 | 0 | 0.5 |
| Comparative Example 3 | 11 | vapor-deposited TiOPc | Comparative Compound 2 | 380 | 20 | 0.9 |
| Comparative Example 4 | 12 | vapor-deposited TiOPc | Comparative Compound 3 | 24 | 2 | 0.8 |
| Comparative Example 5 | 13 | vapor-deposited TiOPc | Comparative Compound 4 | 946 | 58 | 2.2 |

TABLE 3

|  | Photoreceptor No. | Charge-generating material | Charge-transporting material | $V_0$ (–V) | $V_{R10}$ (–V) | $E_{1/2}$ (lux · sec) |
| --- | --- | --- | --- | --- | --- | --- |
| Application Example 9 | 14 | τ-$H_2$Pc | Exemplified Compound 2 | 770 | 0 | 1.0 |
| Application Example 10 | 15 | " | Exemplified Compound 5 | 782 | 2 | 1.1 |
| Application Example 11 | 16 | " | Exemplified Compound 13 | 784 | 4 | 1.0 |
| Application Example 12 | 17 | " | Exemplified Compound 17 | 632 | 2 | 0.9 |
| Application Example 13 | 18 | " | Exemplified Compound 27 | 766 | 2 | 1.0 |
| Comparative Example 6 | 19 | " | Comparative Compound 4 | 66.5 | 5.1 | 1.8 |
| Application Example 14 | 20 | x-$H_2$Pc | Exemplified Compound 1 | 820 | 2 | 1.4 |
| Application Example 15 | 21 | " | Exemplified Compound 2 | 748 | 2 | 1.3 |
| Application Example 16 | 22 | " | Exemplified | 770 | 4 | 1.1 |

TABLE 3-continued

|  | Photo-receptor No. | Charge-generating material | Charge-transporting material | $V_0$ (−V) | $V_{R10}$ (−V) | $E_{1/2}$ (lux · sec) |
|---|---|---|---|---|---|---|
| Application Example 17 | 23 | " | Exemplified Compound 13 | 518 | 4 | 1.2 |
| Application Example 18 | 24 | " | Exemplified Compound 18 | 736 | 0 | 1.0 |
| Comparative Example 7 | 25 | x-$H_2$Pc | Comparative Compound 27 | 924 | 2 | 1.5 |
| Application Example 19 | 26 | crystalline TiOPc | Exemplified Compound 4 | 666 | 6 | 0.8 |
| Application Example 20 | 27 | crystalline TiOPc | Exemplified Compound 1 | 520 | 0 | 0.7 |
| Application Example 21 | 28 | crystalline TiOPc | Exemplified Compound 2 | 880 | 2 | 0.9 |
| Comparative Example 8 | 29 | crystalline TiOPc | Comparative Compound 5 | 70 | 4 | 12.0 |

COMPARATIVE EXAMPLE 7

A photoreceptor 25 was produced in the same manner as in Application Examples 14 to 18 except that Comparative Compound 4 synthesized in Synthesis Example 4 was used in place of Exemplified Compounds 1, 2, 13, 18, and 27. Its electrophotographic properties were examined in the same manner as in Application Examples 1 to 4. The results obtained are shown in Table 3.

APPLICATION EXAMPLES 19 TO 21

In accordance with the method described in JP-A-1-291256, 40 parts by weight of crystalline oxotitanium phthalocyanine was added to a binder resin solution obtained by dissolving 35 parts by weight of a butyral resin (Poly(vinyl butyral) BM-1, manufactured by Sekisui Chemical Co., Ltd.) in 1,425 parts by weight of tetrahydrofuran, and the pigment was dispersed by treating the mixture with an oscillating mill for 2 hours along with glass beads. This dispersion was applied with a wire-wound bar on a sheet obtained by vapor-depositing aluminum on a poly(ethylene terephthalate) (PET) film, and the coating was dried to form a charge-generating layer about 0.5 μm thick. Further, 1 part by weight of each of Exemplified Compounds 1, 2, and 5 synthesized in Examples 1 to 3 and 1 part by weight of a polycarbonate resin (Polycarbonate Z, manufactured by Mitsubishi Gas Chemical Company, Inc.) were mixed in 8 parts by weight of dichloroethane to dissolve them. Each of these solutions was applied on the charge-generating layer with a doctor blade and dried at 80° C. for 2 hours to prepare photoreceptors 26 to 28. The photoreceptors thus obtained were examined for electrophotographic properties in the same manner as in Application Examples 1 to 4. The results obtained are summarized in Table 3.

COMPARATIVE EXAMPLE 8

A photoreceptor 29 was produced in the same manner as in Application Examples 19 to 21 except that Comparative Compound 4 synthesized in Synthesis Example 4 was used in place of Exemplified Compounds 1, 2, and 5. Its electrophotographic properties were examined in the same manner as in Application Examples 1 to 4. The results obtained are given in Table 3.

The results show that the photoreceptors 26 to 28 each employing a compound of this invention have higher potentials after charging and higher sensitivity than the photoreceptor 29 produced in Comparative Example 8.

APPLICATION EXAMPLES 22 TO 27

One part by weight of each of Exemplified Compounds 1, 2, 5, 13, 18, and 27 synthesized in Examples 1 to 6 and 1 part by weight of polycarbonate resin were mixed in 8 parts by weight of dichloroethane to dissolve them. Each of these solutions was applied with a doctor blade on a sheet obtained by vapor-depositing aluminum on a poly(ethylene terephthalate) (PET) film, and the coating was dried at 80° C. for 2 hours. Further, a translucent gold electrode was formed on the charge-transporting layer by vapor deposition to measure the carrier mobility. The measurement of carrier mobility was made by the time-of-flight method (Toshiaki Tanaka, Yasuhiro Yamaguchi, and Masaaki Yokoyama, *Denshi-Shashin*, 29, 366(1990)) using as an illuminant a nitrogen gas laser having a pulse half width of 0.9 nsec and a wavelength of 337 nm. The results obtained at 25° C. and 25 V/μm are given in Table 4.

COMPARATIVE EXAMPLE 9

A film was produced and carrier mobility was measured in the same manner as in Application Examples 22 to 27 except that Comparative Compound 4 synthesized in Synthesis Example 4 was used in place of Exemplified Compounds 1, 2, 5, 13, 18, and 27. The results obtained are given in Table 4.

Table 4 clearly shows that Compounds 1, 2, 5, 13, 18, and 27 according to the present invention have higher carrier mobilities than Comparative Compound 4.

TABLE 4

|  | Charge-transporting material | Carrier mobility μ ($cm^2V^{-1}S^{-1}$) |
|---|---|---|
| Application Example 22 | Exemplified Compound 1 | $20.6 \times 10^{-6}$ |
| Application Example 23 | Exemplified Compound 2 | $16.4 \times 10^{-6}$ |
| Application Example 24 | Exemplified Compound 5 | $14.2 \times 10^{-6}$ |
| Application Example 25 | Exemplified Compound 13 | $35.4 \times 10^{-6}$ |
| Application Example 26 | Exemplified Compound 18 | $22.6 \times 10^{-6}$ |
| Application Example 27 | Exemplified Compound 27 | $10.3 \times 10^{-6}$ |
| Comparative Example 9 | Comparative Compound 4 | $1.32 \times 10^{-6}$ |

APPLICATION EXAMPLE 28

Exemplified Compound 5 was mixed with a 4-fold amount (by weight) of dichloroethane. As a result, the compound was wholly dissolved to give a homogeneous solution, showing that the charge-transporting material had high solubility. This solution was applied, in the same manner as in Application Examples 22 to 27, on a sheet obtained by vapor-depositing aluminum on a poly(ethylene terephthalate) (PET) film and the coating was dried at 80° C. for 2 hours. Although a charge-transporting layer containing the charge-transporting material at a high concentration was thus formed, the layer was homogeneous and free from crystallization and pinhole formation. A translucent gold electrode was then formed on the charge-transporting layer by vapor deposition to measure the carrier mobility. As a result, even when a film consisting only of a compound of the invention was formed, the film could be homogeneous, stable, and thin and attain a carrier mobility as high as $56.7 \times 10^{-6}$ (cm$^2$/Vs), demonstrating that the compound of this invention is extremely useful.

APPLICATION EXAMPLES 29 TO 31

A charge-generating layer was prepared in the same manner as in Application Examples 1 to 4 by using CDB. Further, as a charge-transporting material 1 part by weight of each of the Exemplified Compounds 1, 2, and 5 synthesized in Examples 1 to 3 and 1 part by weight of a bisphenol A/bisphenol copolycarbonate resin (manufactured by Idemitsu Kosan Co., Ltd.) having the following structural formula instead of the polycarbonate resin used in Application Examples 1 to 4 were mixed in 8 parts by weight of dichloroethane to dissolve them. Each of these solutions was applied on the charge-generating layer with a doctor blade and dried at 80° C. for 3 hours. Thus, photoreceptors 30 to 32 were produced.

Bisphenol A/bisphenol copolycarbonate resin

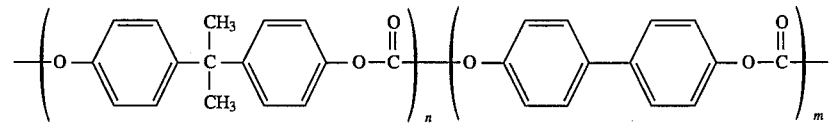

[n/(m + n) = 0.85 wherein m and n each represents a molar number of the repeating unit]

Their electrophotographic properties were examined in the same manner as in Application Examples 1 to 4. The results obtained are summarized in Table 5.

COMPARATIVE EXAMPLE 10

Photoreceptor 33 was produced and examined for electrophotographic properties in the same manner as in Application Examples 29 to 31 except that Comparative Compound 1 synthesized in Synthesis Example 1 was used in place of Exemplified Compounds 1, 2, and 5. The results obtained are summarized in Table 5.

A comparison between Application Examples 29 to 31 and Comparative Example 10 clearly shows that the photoreceptors 30 to 32 employing compounds of this invention each has a small half-decay exposure ($E_{1/2}$), high sensitivity and lower residual potentials ($V_{R10}$), thus demonstrating that the compounds of this invention are effective as an electrophotographic photoreceptor material.

APPLICATION EXAMPLES 32 TO 34

A charge-generating layer was prepared in the same manner as in Application Examples 5 to 8 comprising vacuum deposition of oxotitanium phthalocyanine (TiOPc). Further, 1 part by weight of each of the Exemplified Compounds 1, 2, and 5 synthesized in Examples 1, 2, and 3 and 1 part by weight of the bisphenol A/bisphenol copolycarbonate resin used in Application Examples 29 to 31 were mixed in 8 parts by weight of dichloroethane to dissolve them. Each of these solutions was applied on the charge-generating layer with a doctor blade and dried at 80° C. for 3 hours. Thus, photoreceptors 34 to 36 were produced. Their electrophotographic properties were examined in the same manner as in Application Examples 1 to 4. The results obtained are summarized in Table 5.

COMPARATIVE EXAMPLE 11

A charge-generating layer was prepared in the same manner as in Application Examples 5 to 8 comprising vacuum deposition of oxotitanium phthalocyanine (TiOPc). Further, 1 part by weight of the Comparative Compound 4 synthesized in Synthesis Example 4 and 1 part by weight of the bisphenol A/bisphenol copolycarbonate resin used in Application Examples 29 to 31 were mixed in 8 parts by weight of dichloroethane to dissolve them. This solution was applied on the charge-generating layer with a doctor blade and dried at 80° C. for 3 hours. Thus, photoreceptor 37 was produced. Its electrophotographic properties were examined in the same manner as in Application Examples 1 to 4. The results obtained are summarized in Table 5.

A comparison between Application Examples 32 to 34 and Comparative Example 11 clearly shows that the photoreceptors 34 to 36 employing compounds of this invention each has a small half-decay exposure ($E_{1/2}$), high sensitivity and lower residual potentials ($V_{R10}$), thus demonstrating that the compounds of this invention are effective as an electrophotographic photoreceptor material.

TABLE 5

| | Photo-receptor No. | Charge-generating material | Charge-transporting material | $V_0$ (-V) | $V_{R10}$ (-V) | $E_{1/2}$ (lux·sec) |
|---|---|---|---|---|---|---|
| Application Example 29 | 30 | CDB | Exemplified Compound 1 | 1100 | 4 | 4.1 |
| Application Example 30 | 31 | " | Exemplified Compound 2 | 964 | 0 | 3.1 |
| Application Example 31 | 32 | " | Exemplified Compound 5 | 1000 | 0 | 2.7 |
| Comparative Example 10 | 33 | " | Comparative Compound 1 | 1228 | 18 | 5.3 |
| Application Example 32 | 34 | vapor-deposited TiOPc | Exemplified Compound 1 | 942 | 0 | 0.7 |
| Application Example 33 | 35 | vapor-deposited TiOPc | Exemplified Compound 2 | 966 | 0 | 0.8 |
| Application Example 34 | 36 | vapor-deposited TiOPc | Exemplified Compound 5 | 856 | 0 | 0.6 |
| Comparative Example 11 | 37 | vapor-deposited TiOPc | Comparative Compound 4 | 1160 | 20 | 1.1 |

APPLICATION EXAMPLES 35 TO 37

A charge-generating layer was prepared in the same manner as in Application Examples 9 to 13 using τ-form metal-free phthalocyanine (τ-H$_2$Pc). Further, 1 part by weight of each of the Exemplified Compounds 1, 2, and 5 synthesized in Examples 1, 2, and 3 and 1 part by weight of the bisphenol A/bisphenol copolycarbonate resin used in Application Examples 29 to 31 were mixed in 8 parts by weight of dichloroethane to dissolve them. Each of these solutions was applied on the charge-generating layer with a doctor blade and dried at 80° C. for 2 hours. Thus, photoreceptors 38 to 40 were produced. Their electrophotographic properties were examined in the same manner as in Application Examples 1 to 4. The results obtained are summarized in Table 6.

APPLICATION EXAMPLE 38

A charge-generating layer was prepared in the same manner as in Application Examples 14 to 18 using x-form metal-free phthalocyanine (x-H$_2$Pc). Further, 1 part by weight of the Exemplified Compound 2 and 1 part by weight of the bisphenol A/bisphenol copolycarbonate resin used in Application Examples 29 to 31 were mixed in 8 parts by weight of dichloroethane to dissolve them. This solution was applied on the charge-generating layer with a doctor blade and dried at 80° C. for 2 hours. Thus, photoreceptor 41 was produced. Its electrophotographic properties were examined in the same manner as in Application Examples 1 to 4. The results obtained are summarized in Table 6.

COMPARATIVE EXAMPLE 12

A charge-generating layer was prepared in the same manner as in Application Examples 14 to 18 using x-form metal-free phthalocyanine (x-H2Pc). Further, 1 part by weight of the Comparative Compound 4 and 1 part by weight of the bisphenol A/bisphenol copolycarbonate resin used in Application Examples 29 to 31 were mixed in 8 parts by weight of dichloroethane to dissolve them. This solution was applied on the charge-generating layer with a doctor blade and dried at 80° C. for 2 hours. Thus, photoreceptor 42 was produced. Its electrophotographic properties were examined in the same manner as in Application Examples 1 to 4. The results obtained are summarized in Table 6.

A comparison between Application Example 38 and Comparative Example 12 clearly shows that the photoreceptor 41 employing the compound of this invention has a small half-decay exposure ($E_{1/2}$), high sensitivity and lower residual potentials ($V_{R10}$), thus demonstrating that the compounds of this invention are effective as an electrophotographic photoreceptor material.

APPLICATION EXAMPLES 39 AND 40

A charge-generating layer was prepared in the same manner as in Application Examples 19 to 21 using crystalline oxotitanium phthalocyanine. Further, 1 part by weight of the Exemplified Compounds 1 and 2 and 1 part by weight of the bisphenol A/bisphenol copolycarbonate resin used in Application Examples 29 to 31 were mixed in 8 parts by weight of dichloroethane to dissolve them. Each of these solutions was applied on the charge-generating layer with a doctor blade and dried at 80° C. for 2 hours. Thus, photoreceptors 43 and 44 were produced. Their electrophotographic properties were examined in the same manner as in Application Examples 1 to 4. The results obtained are summarized in Table 6.

COMPARATIVE EXAMPLE 13

A charge-generating layer was prepared in the same manner as in Application Examples 19 to 21 using crystalline oxotitanium phthalocyanine. Further, 1 part by weight of the Comparative Compound 4 and 1 part by weight of the bisphenol A/bisphenol copolycarbonate resin used in Application Examples 29 to 31 were mixed in 8 parts by weight of dichloroethane to dissolve them. This solution was applied on the charge-generating layer with a doctor blade and dried at 80° C. for 2 hours. Thus, photoreceptor 45 was produced. Its electrophotographic properties were examined in the same manner as in Application Examples 1 to 4. The results obtained are summarized in Table 6.

TABLE 6

| Photo-receptor No. | Charge-generating material | Charge-transporting material | $V_0$ (–V) | $V_{R10}$ (–V) | $E_{1/2}$ (lux · sec) |
|---|---|---|---|---|---|
| Application Example 35 | 38 | τ-$H_2$Pc | Exemplified Compound 2 | 960 | 0 | 1.0 |
| Application Example 36 | 39 | " | Exemplified Compound 1 | 880 | 8 | 1.0 |
| Application Example 37 | 40 | " | Exemplified Compound 5 | 964 | 0 | 1.2 |
| Application Example 38 | 41 | x-$H_2$Pc | Exemplified Compound 2 | 678 | 0 | 1.3 |
| Comparative Example 12 | 42 | x-$H_2$Pc | Comparative Compound 4 | 1074 | 16 | 1.6 |
| Application Example 39 | 43 | crystalline TiOPc | Exemplified Compound 1 | 860 | 4 | 0.5 |
| Application Example 40 | 44 | crystalline TiOPc | Exemplified Compound 2 | 790 | 6 | 0.7 |
| Comparative Example 13 | 45 | crystalline TiOPc | Comparative Compound 4 | 670 | 16 | 1.0 |

APPLICATION EXAMPLES 41 TO 46

Charge-transporting layers were prepared in the same manner as in Application Examples 22 to 27 respectively except that 1 part by weight of the bisphenol A/bisphenol copolycarbonate resin used in Application Examples 29 to 31 was used in place of the polycarbonate resin (Polycarbonate Z). The thus obtained charge-transporting layers were dried at 80° C. for 2 hours to produce films. With respect to the obtained films, carrier mobility was measured in the same manner as in Application Examples 22 to 27 using the time-of-flight method. The results obtained at 25° C. and 25 V/μm are given in Table 7.

COMPARATIVE EXAMPLE 14

A charge-transporting layer was prepared in the same manner as in Application Examples 22 to 27 except that 1 part by weight of the bisphenol A/bisphenol copolycarbonate resin used in Application Examples 29 to 31 was used in place of the polycarbonate resin (Polycarbonate Z). The thus obtained charge-transporting layer was dried at 80° C. for 2 hours to produce a film. With respect to the obtained film, carrier mobility was measured in the same manner as in Application Examples 22 to 27 using the time-of-flight method. The results obtained at 25° C. and 25 V/μm are given in Table 7.

TABLE 7

| | Charge-transporting material | Carrier mobility μ ($cm^2V^{-1}S^{-1}$) |
|---|---|---|
| Application Example 41 | Exemplified Compound 1 | $37.5 \times 10^{-6}$ |
| Application Example 42 | Exemplified Compound 2 | $37.1 \times 10^{-6}$ |
| Application Example 43 | Exemplified Compound 5 | $119 \times 10^{-6}$ |
| Application Example 44 | Exemplified Compound 13 | $58.8 \times 10^{-6}$ |
| Application Example 45 | Exemplified Compound 18 | $37.5 \times 10^{-6}$ |
| Application Example 46 | Exemplified Compound 27 | $50.8 \times 10^{-6}$ |
| Comparative Example 14 | Comparative Compound 4 | $2.43 \times 10^{-6}$ |

EXAMPLE 7

Synthesis of Exemplified Compound 1 (n=0, $R^1,R^2,R^3,R^4,R^5$=H)

(1) Synthesis of 4'-(4",4"-diphenyl-1",3"-butadienyl)-4-formyl-triphenylamine (13a; $R^1,R^2,R^5$=H)

Into a 1-liter reaction flask were introduced in a nitrogen atmosphere 54.8 g (0.166 mol) of diethyl 3,3-diphenylallylphosphite (6a), 50.0 g (0.166 mol) of 4,4'-diformyltriphenylamine (8a), and 300 ml of DMF dried with a molecular sieve to dissolve them. Subsequently, 20 g (0.178 mol) of potassium tert-butoxide was added little by little while stirring at 5°–10° C. over 10 minutes, and then the solution was stirred at room temperature for 1 hour. The reaction mixture was poured into 3 liters of ice water and then subjected to extraction with toluene, liquid separation, washing with water, drying with magnesium sulfate, and concentration to obtain 76.3 g of a crude product. This product was purified by silica gel chromatography (eluent: benzene/ethyl acetate=9/1 by volume), giving 19.8 g of the titled compound.

Theoretical yield, 25.0%

Spectral data for this compound are as follows.

MASS spectrum (m/e): 477($M^+$), 286, 203, 168, 91

$^1$H-NMR spectrum (400 MHz, $CDCl_3$, δ ppm): 6.70(d, J=14.0 Hz, 1H), 6.82 (d, J=10.8 Hz, 1H), 6.85–6.90(m, 1H), 7.00–7.44 (m, 13H), 7.68 (d, J=8.8 Hz, 2H), 9.85 (s, 1H)

(2) Synthesis of 4-(4",4"-diphenyl-1",3"-butadienyl)-4'-(2'",2'"-diphenylvinyl)triphenylamine (Exemplified Compound 1; n=0, $R^1,R^2,R^3,R^4,R^5$=H)

Into a 100-ml reaction flask were introduced 3.91 g (8.2 mmol) of 4'-(4",4"-diphenyl-1",3"-butadienyl)-4-formyltriphenylamine (13a, $R^1,R^2,R^5$=H), 2.95 g (9.7 mmol) of diethyl diphenylmethylphosphite (10a), and 37 ml of dry DMF. The contents were stirred at room temperature to completely dissolve them. Subsequently, 1.09 g (9.7 mmol) of potassium tert-butoxide was added little by little (the mixture heated from 20° to 33° C.), and reaction was conducted at room temperature for 16 hours. The disappearance of the starting materials was ascertained by TLC, before the reaction was terminated.

After cooling, the reaction mixture was poured into 370 ml of methanol, and the resulting precipitate was separated from the liquid by filtration to obtain 5.67 g of crystals. This reaction product was purified by silica gel column chromatography (eluent: benzene/ethyl acetate=9/1 by volume), giving 4.80 g of a purified reaction product. The purified product was recrystallized from a mixed solvent consisting of acetonitrile and ethyl acetate, giving 2.73 g of yellow crystals of the titled compound (Exemplified Compound 1).

Theoretical yield, 52.8%
m.p., 108°–109° C.
Spectral data for this compound are as follows.
$^1$H-NMR spectrum (400 MHz, CDCl$_3$, δ ppm): 6.66 (1H, d, J=15.1 Hz), 6.77 (1H, dd, J=10.7 Hz, 15.1 Hz), 6.80 (1H, d, J=10.7 Hz), 6.87 (2H, d, J=8.7 Hz), 6.90 (1H, s), 6.92 (2H, d, J=8.7 Hz), 7.00–7.05 (3H, m), 7.15 (2H, d, J=8.7 Hz), 7.19–7.42 (22H, m)
MASS (m/e): 627 (M$^+$), 451

EXAMPLE 8

Synthesis of 4-[4",4"-di(p-tolyl)-1",3"-butadienyl]-4'-[2'",2'"-di(m-tolyl)vinyl]triphenylamine (Exemplified Compound 3; n=0, R$^1$,R$^2$=4-Me, R$^3$, R$^4$=3-Me, R$^5$=H)

(1) Synthesis of 4'-[4",4"-di(p-tolyl)-1",3"-butadienyl]-4-formyltriphenylamine (13b; R$^1$,R$^2$=4-Me, R$^5$=H)

Reactions were conducted in the same manner as in (1) in Example 7 except that 59.50 g (0,166 mol) of diethyl 3,3-di(p-tolyl)allyl phosphite (6b) was used in place of diethyl 3,3-diphenylallyl phosphite (6a) and that 4,4-diformyltriphenylamine (8a) was used in an amount of 50.0 g (0.166 mol). As a result, 24.3 g of a crude product was obtained. This product was recrystallized from a mixture solvent consisting of acetonitrile and ethyl acetate, giving 16.5 g of yellow crystals of the compound (13b).

Theoretical yield, 19.7%
m.p., 143°–145° C.
Spectral data for this compound are as follows.
MASS spectrum (m/e): 505(M$^+$), 286, 168
$^1$H-NMR spectrum (400 MHz, δ; ppm in CDCl$_3$): 2.35 (s, 3H), 2.40 (s, 3H), 6.67 (d, J=14.4 Hz, 1H), 6.79–6.90 (m, 2H), 7.00–7.07 (m, 4H), 7.08–7.37 (m, 15H), 7.67 (d, J=8.9 Hz, 2H), 9.80 (s, 1H)

(2) Synthesis of 4-[4",4"-di(p-tolyl)-1",3"-butadienyl]-4'-[2'",2'"-di(m-tolyl)vinyl]triphenylamine (Exemplified Compound 3)

3.5 g (6.92 mmol) of 4'-[4",4"-di(p-tolyl)-1",3"-butadienyl]-4-formyltriphenylamine (13b) and 2.53 g (7.61 mmol) of diethyl di(m-tolyl)methyl phosphite (10b, R$^3$,R$^4$=3-Me) Me) were dissolved in 30 ml of DMF, and the reaction and post treatment were conducted in the same manner as in (2) in Example 7 by using 0.9 g (8.02 mmol) of potassium-t-butoxide as a base to obtain 2.53 g of Exemplified Compound 3.

Theoretical yield, 88.7%
Spectral data for this compound are as follows.
MASS spectrum (m/e): 683(M$^+$), 464, 342, 282
$^1$H-NMR spectrum (400 MHz, δ; ppm in CDCl$_3$): 2.30 (s, 3H), 2.33 (s, 3H), 2.34 (s, 3H), 2.41 (s, 3H), 6.59–6.67 (m, 1H), 6.77–6.83 (m, 4H), 6.83–6.88 (m, 3H), 6.92 (d, J=8.6 Hz, 2H), 6.97–7.13 (m, 10H), 7.13–7.25 (m, 13H)

EXAMPLE 9

Synthesis of 4-[4",4"-di(p-tolyl)-1",3"-butadienyl]-4'-[2'",2'"-diphenylvinyl]triphenylamine (Exemplified Compound 31; n=0, R$^1$,R$^2$=4-Me R$^3$,R$^4$,R$^5$=H )

(1) Synthesis of 4-formyl-4'-(2",2"-diphenylvinyl)triphenylamine

Reaction was conducted in the same manner as in (1) in Example 7 except that 50.5 g (0.166 mol) of diethyl diphenylmethyl phosphite (10a) was used in place of diethyl 3,3-diphenylallylphosphite (6a). Thus, 21.1 g of 4-formyl-4'-(2",2"-diphenylvinyl)triphenylamine was obtained.

Theoretical yield, 28.1%; m.p., 49°–50° C.
Spectral data for this compound are as follows.
Mass spectrum (m/e); 451(M$^+$), 78
$^1$H-NMR spectrum (400 MHz, δ; ppm in CDCl$_3$): 6.87–7.03 (m, 6H), 7.08–7.18 (m, 3H), 7.20–7.38 (m, 13H), 7.66 (d, J=8.8 Hz, 2H), 9.81 (s, 1H)

(2) Synthesis of 4-[4",4"-di(p-tolyl)-1",3"-butadienyl]-4'-[2'",2'"-diphenylvinyl]triphenylamine (Exemplified Compound 31)

In the same manner as in (2) in Example 7, 3.91 g of Exemplified Compound 31 was obtained from 3.0 g (6.53 mmol) of 4-formyl-4'-(2",2"-diphenylvinyl)triphenylamine (12a; R$^3$,R$^4$,R$^5$=H), 2.58 g (7.18 mmol) of diethyl 3,3-di(p-tolyl)allylphosphite, 0.97 g (8.64 mmol) of potassium-t-butoxide, and 30 ml of DMF.

Theoretical yield, 90.4%; m.p., 124°–125° C.
Spectral data for this compound are as follows.
Mass spectrum (m/e); 655(M$^+$), 436, 179, 43
$^1$H-NMR spectrum (400 MHz, δ; ppm in CDCl$_3$): 2.34 (s, 3H), 2.40 (s, 3H), 6.59–6.67 (m, 1H), 6.76–6.95 (m, H), 6.95–7.37 (m, 25H)

EXAMPLE 10

Synthesis of 4-(4",4"-diphenyl-1",3"-butadienyl)-4'-[4'",4'"-di(p-tolyl)-1'",3'"-butadienyl]triphenylamine (Exemplified Compound 36; n=1, R$^1$,R$^2$=4-Me R$^3$,R$^4$,R$^5$=H)

In the same manner as in (2) in Example 7, 4.71 g of Exemplified Compound 36 was obtained from 3.5 g (6.92 mmol) of 4'-[4",4"-di(p-tolyl)-1",3"-butadienyl]-4-formyltriphenylamine (13b), 2.52 g (7.63 mmol) of diethyl 3,3-diphenylallylphosphite (6a), 0.9 g (8.02 mmol) of potassium-t-butoxide, and 30 ml of DMF.

Theoretical yield, 99.8%
Spectral data for this compound are as follows.
Mass spectrum (m/e); 681(M$^+$), 16
$^1$H-NMR spectrum (400 MHz, δ; ppm in CDCl$_3$): 2.35 (s, 3H), 2.40 (s, 3H), 6.60–6.69 (m, 2H), 6.75–6.88 (m, 4H), 6.93–7.12 (m, 6H), 7.10–7.32 (m, 19H), 7.32–7.43 (m, 3H)

In addition, minor peaks of 6.22 (t, J=11.6 Hz) and 6.38 (d, J=11.6 Hz) were observed (cis-double bond).

EXAMPLE 11

Synthesis of Exemplified Compound 41 (n=0, R$^1$,R$^2$=2, 2'-ethylene, R$^3$,R$^4$,R$^5$=H)

(1) Synthesis of 10,11-dihydro-5-methylene-5H-dibenzo[a,b]cycloheptene (4c)

Into a four-necked flask were introduced 13.8 g (0.576 mol) of magnesium and 500 ml of dry THF. Slight amounts of iodine and methyl iodide were further added, following which the initiation of reaction was ascertained. Then, methyl chloride gas was bubbled into the mixture while the mixture was maintained at 20° to 30° C. for 4 hours to complete the preparation of a Grignard reagent.

To this reaction mixture was added dropwise a liquid mixture of 100 g (0.48 mol) of dibenzosuberone and 300 ml of dry toluene over a period of 2 hours. Reaction was thereafter conducted at room temperature for 5 hours. The disappearance of dibenzosuberone was ascertained by gas chromatography, before the reaction was terminated.

After ice cooling, the reaction mixture was poured into a dilute hydrochloric acid for hydrolysis. The hydrolyzed reaction mixture was subjected to liquid separation, and the aqueous layer was extracted with toluene, and then mixed into the organic layer. Further, this solution was neutralized with an aqueous saturated sodium bicarbonate and washed with water.

After concentrating, 500 ml of toluene and 0.5 g of p-toluene sulfonic acid were further added to the resulting solution, and azeotropic dehydration was conducted with reflux stirring. After cooling, the mixture was neutralized with an aqueous saturated sodium bicarbonate, washed with water, dried with sodium sulfate anhydride, and concentrated and distilled to obtain 92.3 g of a crude reaction product (b.p., 137° C./1 mmHg). This reaction product was recrystallized from hexane, giving 84.2 g of 10,11-dihydro-5-methylene-5H-dibenzo[a,b]cycloheptene (4c) (theoretical yield, 85.1%). m.p., 68–69° C.

Spectral data for this compound are as follows.

Mass spectrum (m/e); 206($M^+$), 219,203, 178, 141, 115, 91, 23

NMR spectrum (400 MHz, $CDCl_3$, δ ppm): 3.05 (s, 4H), 5.42 (s, 2H), 7.09–7.23 (m, 6H), 7.35 (m, 2H)

(2) Synthesis of 5-(2-chloroethylidene)-10,11-dihydro-5H-dibenzo[a,d]cycloheptene (5c):

In the same manner as in (2) in Example 2, hydrogen chloride gas was bubbled into the mixture of 20.6 g (0.1 mol) of 10,11-dihydro-5-methylene-5H-dibenzo[a,d]cycloheptene (4c), 41 g of acetic acid, and 4.5 g (0.15 mol) of paraformaldehyde. After reaction was conducted, the reaction product was extracted with toluene, neutralized with a saturated sodium bicarbonate solution, and washed with water. Further, this product was dried with sodium sulfate anhydride, concentrated and then recrystallized from hexane to obtain 23.4 g of the compound (5c).

Theoretical yield, 92.0%; m.p., 103°–104° C.

Spectral data for this compound are as follows.

Mass spectrum (m/e); 254($M^+$), 219, 203, 141,115, 91,

NMR spectrum (400 MHz, $CDCl_3$, δ ppm): 2.70–3.05 (brs, 2H), 3.20–3.45 (brs, 2H), 4.12 (d, J=8.1 Hz, 2H), 6.07 (t, J=8.1 Hz, 1H), 7.08 (m, 1H), 7.12–7.30 (m, 6H), 7.34 (m, 1H)

(3) Synthesis of diethyl β-(10,11-dihydro-5H-dibenzo[a,d]cycloheptenylidene-5)-ethylphosphite (6c):

20 g (0.0786 mol) of 5-(2-chloroethylidene)-10,11-dihydro-5H-dibenzo[a,d]cycloheptene (5c) and 65 g (0.393 mol) of triethylphosphite were stirred with refluxing for 10 hours. The disappearance of the compound (5c) was ascertained by gas chromatography and then triethylphosphite was distilled under reduced pressure to obtain 27.8 g of the residue. Theoretical yield, 99.2%

Spectral data for this compound are as follows.

Mass spectrum (m/e); 356($M^+$), 191, 125

NMR spectrum (400 MHz, $CDCl_3$, δ ppm): 1.28 (m, 6H), 2.67 (d, J=8.1 Hz, 1H), 2.75 (d, J=8.1 Hz, 1H), 2.70 (m, 1H), 2.95 (m, 1H), 3.25–3.48 (m, 2H), 3.93–4.18 (m, H), 5.90 (q, J=7.9 Hz, 1H), 7.05 (m, 1H), 7.10–7.31 (m, 7H)

(4) Synthesis of Exemplified Compound 41:

In the same manner as in (2) in Example 7, 4.23 g of Exemplified Compound 41 was obtained from 3.0 g (6.53 mmol) of 4-formyl-4'-(2",2"-diphenylvinyl)triphenylamine (12a), 2.65 g (7.19 mmol) of diethyl β-(10,11-dihydro-5H-dibenzo[a,d]cycloheptinylidene-5)-ethylphosphite (6c), 30 ml of dry DMF, and 0.97 g (8.64 mmol) of potassium-t-butoxide. Theoretical yield, 97.2%

Spectral data for this compound are as follows. Mass spectrum (m/e); 653($M^+$), 436, 191, 73, 43

NMR spectrum (400 MHz, $CDCl_3$, δ ppm): 2.70–3.50 (brs, 4H), 6.60–6.67 (m, 2H), 6.75–6.94 (m, 8H), 6.97–7.09 (m, 4H), 7.13–7.40 (m, 21H)

In addition, minor peaks of 6.24 (t, J=11.5 Hz) and 6.33 (d, J=11.5 Hz) were observed (cis-double bond).

EXAMPLE 12

Synthesis of Exemplified Compound 42 (n=1, $R^1,R^2$=2, 2'-ethylene, $R^3,R^4,R^5$=H )

In the same manner as in (2) in Example 7,570 mg of Exemplified Compound 42 was obtained from 1.3 g (2.72 mmol) of 4'-(4",4"-diphenyl-1",3"-butadienyl)-4-formyltriphenylamine (13a), 1.1 g (3.09 mmol) of diethyl β-(10, 11-dihydro-5H-dibenzo[a,d]cycloheptylinidene-5)-ethylphosphite (6c), 10 ml of DMF, and 330 mg (2.94 mmol) of potassium-t-butoxide.

Theoretical yield, 29.4%; m.p., 125°–130° C.

Spectral data for this compound are as follows.

Mass spectrum (m/e); 679($M^+$), 462

NMR spectrum (400 MHz, $CDCl_3$, δ ppm): 2.70–3.45 (brs, 4H), 6.60–6.71 (m, 3H), 6.74–6.83 (m, 3H), 6.83–7.43 (m, 31H)

In addition, minor peaks of 6.20–6.37 (m) was observed (cis-double bond).

APPLICATION EXAMPLES 47 AND 48

Photoreceptors 46 and 47 were produced in the same manner as in Application Examples 1 to 4 except that Exemplified Compounds 31 and 42 were used respectively in place of Exemplified Compounds 2, 5, 13 and 18, and bisazo compound (20) was used in place of CDB. Their electrophotographic properties were examined in the same manner as in Application Examples 1 to 4. The results obtained are shown in Table 8.

APPLICATION EXAMPLE 49

A photoreceptor 48 was produced in the same manner as in Application Examples 9 to 13 except that Exemplified Compound 42 was used in place of Exemplified Compounds 2, 5, 13 and 18. Its electrophotographic properties were examined in the same manner as in Application Examples 1 to 4. The results obtained are shown in Table 8.

APPLICATION EXAMPLE 50

A photoreceptor 49 was produced in the same manner as in Application Examples 14 to 18 except that Exemplified Compound 36 was used in place of Exemplified Compounds 1, 2, 13, 18 and 27. Its electrophotographic properties were examined in the same manner as in Application Examples 1 to 4. The results obtained are shown in Table 8.

APPLICATION EXAMPLES 51 AND 52

Photoreceptors 50 and 51 were produced in the same manner as in Application Examples 19 to 21 except that Exemplified Compounds 31 and 36 were used respectively in place of Exemplified Compounds 1, 2 and 5, and crystalline oxotitanium phthalocyanine synthesized by the method of JP-A-63-20365 was used in place of the crystalline oxotitanium phthalocyanine. Their electrophotographic properties were examined in the same manner as in Application Examples 1 to 4. The results obtained are shown in Table 8.

APPLICATION EXAMPLES 53 and 54

Carrier mobility was measured in the same manner as in Application Examples 22 to 27 except that Exemplified Compounds 36 and 42 were used respectively in place of Exemplified Compounds 1, 2, 5, 13, 18, and 27. The results obtained are given in Table 9.

TABLE 8

|  | Photo-receptor No. | Charge-generating material | Charge-transporting material | $V_0$ (−V) | $V_{R10}$ (−V) | $E_{1/2}$ (lux · sec) |
|---|---|---|---|---|---|---|
| Application Example 47 | 46 | bisazo compound (20) | Exemplified Compound 31 | 1320 | 0 | 1.2 |
| Application Example 48 | 47 | bisazo compound (20) | Exemplified Compound 42 | 1360 | 0 | 2.3 |
| Application Example 49 | 48 | τ-H$_2$Pc | Exemplified Compound 42 | 1086 | 0 | 1.1 |
| Application Example 50 | 49 | x-H$_2$Pc | Exemplified Compound 36 | 1096 | 0 | 0.9 |
| Application Example 51 | 50 | TiOPc (dispersion) | Exemplified Compound 31 | 1132 | 2 | 0.8 |
| Application Example 52 | 51 | TiOPc (dispersion) | Exemplified Compound 36 | 740 | 0 | 1.1 |

TABLE 9

|  | Charge-transporting material | Carrier mobility μ (cm$^2$V$^{-1}$S$^{-1}$) |
|---|---|---|
| Application Example 53 | Exemplified Compound 36 | 33.6 × 10$^{-6}$ |
| Application Example 54 | Exemplified Compound 42 | 18.4 × 10$^{-6}$ |

While the invention has been described in detail and with reference to specific embodiments thereof, it will be apparent to one skilled in the art that various changes and modifications can be made therein without departing from the spirit and scope thereof.

What is claimed is:

1. An electrophotographic photoreceptor containing a charge generating material and a charge-transporting layer comprising a triphenylamine derivative represented by the following general formula (1):

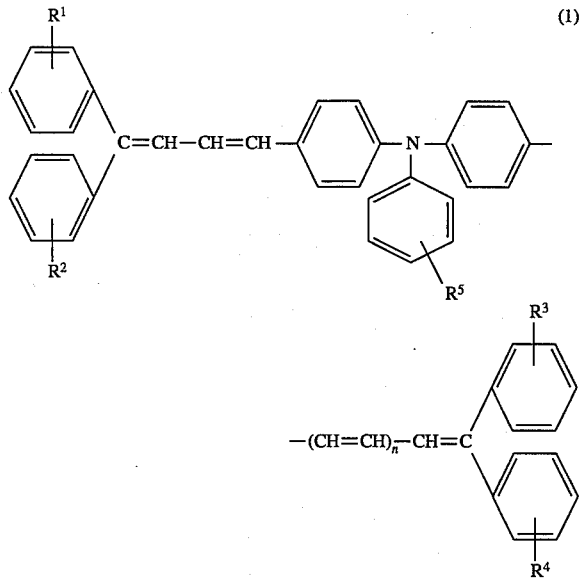

wherein $R^1$, $R^2$, $R^3$, $R^4$, and $R^5$ may be the same or different and each represents a hydrogen atom, a lower alkyl group, an alkoxy group, a halogen atom, or an aryl group which may have a substituent and n represents 0 or 1.

2. An electrophotographic photoreceptor containing (a) a charge-generating layer comprising at least one charge-generating material and
(b) a charge-transporting layer comprising at least one binder and a triphenylamine derivative represented by the following general formula (1):

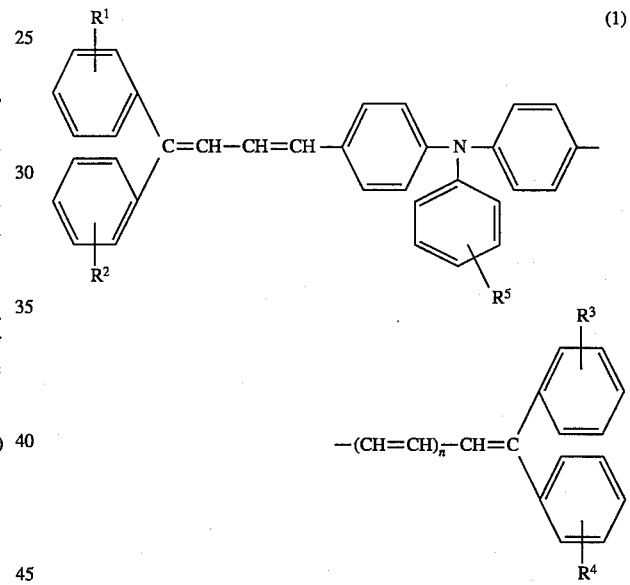

wherein $R^1$, $R^2$, $R^3$, $R^4$, and $R^5$ may be the same or different and each represents a hydrogen atom, a lower alkyl group, an alkoxy group, a halogen atom, or an aryl group which may have a substituent and n represents 0 or 1.

3. An electrophotographic photoreceptor as in claim 2, wherein the charge-generating material is a phthalocyanine pigment.

4. An electrophotographic photoreceptor as in claim 3, wherein the phthalocyanine pigment is selected from the group consisting of TiOPc, τ-H$_2$Pc and x-H$_2$Pc.

5. An electrophotographic photoreceptor as in claim 2, wherein the charge-generating material is an azo pigment.

6. An electrophotographic photoreceptor as in claim 5, wherein the azo pigment is selected from the group consisting of monoazo compound, bisazo compound and trisazo compound.

7. An electrophotographic photoreceptor as in claim 2, wherein the binder is a polycarbonate.

8. An electrophotographic photoreceptor as in claim 7, wherein the polycarbonate is the compound represented by the formula (16):

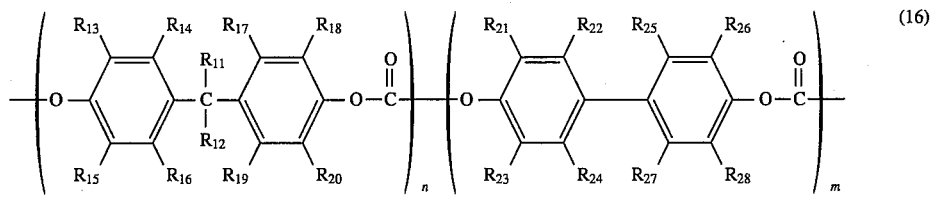

(16)

wherein $R_{11}$ and $R_{12}$ each independently represents a hydrogen atom, an alkyl group or an aryl group, $R_{11}$ and $R_{12}$ may be taken together to form a ring, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$ and $R_{28}$ each independently represents a hydrogen atom, a halogen atom, an alkyl group or an aryl group, and n and m each represents a molar number of the repeating unit, wherein both n and m units are present.

9. An electrophotographic photoreceptor as in claim 8, wherein n is 0.85 and m is 0.15.

* * * * *